(12) United States Patent
Duer

(10) Patent No.: US 8,288,157 B2
(45) Date of Patent: Oct. 16, 2012

(54) WAVEGUIDE-BASED OPTICAL SCANNING SYSTEMS

(75) Inventor: Reuven Duer, Thousand Oaks, CA (US)

(73) Assignee: PLC Diagnostics, Inc., Chatsworth, CA (US)

( * ) Notice: Subject to any disclaimer, the term of this patent is extended or adjusted under 35 U.S.C. 154(b) by 901 days.

(21) Appl. No.: 12/209,295

(22) Filed: Sep. 12, 2008

(65) Prior Publication Data

US 2009/0068668 A1    Mar. 12, 2009

Related U.S. Application Data

(60) Provisional application No. 60/971,878, filed on Sep. 12, 2007.

(51) Int. Cl.
  *C12M 1/34* (2006.01)
(52) U.S. Cl. ............... 435/288.7; 422/82.11; 435/288.4; 435/808; 436/169; 436/172; 436/524; 436/527; 436/805; 436/809
(58) Field of Classification Search .................. None
  See application file for complete search history.

(56) References Cited

U.S. PATENT DOCUMENTS

| | | |
|---|---|---|
| 4,394,060 A | 7/1983 | Verber et al. |
| 4,444,879 A * | 4/1984 | Foster et al. ................. 435/7.95 |
| 4,478,485 A | 10/1984 | Khoe et al. |
| 4,515,430 A | 5/1985 | Johnson |
| 4,651,343 A | 3/1987 | Laor |
| 4,744,623 A | 5/1988 | Prucnal et al. |
| 4,746,179 A | 5/1988 | Dahne et al. |
| 4,799,797 A | 1/1989 | Huggins |
| 4,815,843 A | 3/1989 | Tiefenthaler et al. |
| 4,820,016 A | 4/1989 | Cohen et al. |
| 4,838,631 A | 6/1989 | Chande et al. |
| 4,850,666 A | 7/1989 | Izutsu et al. |
| 4,876,446 A | 10/1989 | Kambe et al. |
| 4,881,789 A | 11/1989 | Levinson |
| 4,889,407 A | 12/1989 | Markle et al. |
| 4,906,837 A | 3/1990 | Doneen et al. |
| 4,940,328 A | 7/1990 | Hartman |
| 4,978,503 A | 12/1990 | Shanks et al. |
| 4,998,792 A | 3/1991 | Boerstler et al. |
| 5,031,987 A | 7/1991 | Norling |
| 5,075,494 A | 12/1991 | Gassen |

(Continued)

FOREIGN PATENT DOCUMENTS

EP        598213 B1    7/1997

(Continued)

OTHER PUBLICATIONS

Ausubel, et al. (Eds.) Current Protocols in Molecular Biology, vols. I, II, and III, (1997).

(Continued)

*Primary Examiner* — Chris L Chin
(74) *Attorney, Agent, or Firm* — Shay Glenn LLP

(57) ABSTRACT

A scanning sensor system, methods of use and kits for detecting a biologically active analyte are provided. The scanning sensor system includes a light source, a detector, a substrate comprising a plurality of waveguides and a plurality of optical sensing sites in optical communication with one or more waveguide of the substrate, and at least one adapter configured to couple with the substrate and provide optical communication between the light source, the waveguides of the substrate, and the detector.

61 Claims, 23 Drawing Sheets

U.S. PATENT DOCUMENTS

| | | |
|---|---|---|
| 5,077,878 A | 1/1992 | Armiento et al. |
| 5,081,012 A | 1/1992 | Flanagan et al. |
| 5,120,131 A | 6/1992 | Lukosz |
| 5,121,457 A | 6/1992 | Foley et al. |
| 5,151,480 A | 9/1992 | Podszun et al. |
| 5,173,747 A | 12/1992 | Boiarski et al. |
| 5,208,111 A | 5/1993 | Decher et al. |
| 5,217,568 A | 6/1993 | Tessier et al. |
| 5,344,784 A | 9/1994 | Attridge |
| 5,377,008 A | 12/1994 | Ridgway et al. |
| 5,439,647 A | 8/1995 | Saini |
| 5,440,388 A | 8/1995 | Erickson |
| 5,444,805 A | 8/1995 | Mayer |
| 5,455,178 A | 10/1995 | Fattinger |
| 5,479,260 A | 12/1995 | Fattinger |
| 5,494,798 A | 2/1996 | Gerdt et al. |
| 5,496,701 A | 3/1996 | Pollard-Knight |
| 5,512,492 A | 4/1996 | Herron et al. |
| 5,547,839 A | 8/1996 | Dower et al. |
| 5,573,956 A | 11/1996 | Hanning |
| 5,577,137 A | 11/1996 | Groger et al. |
| 5,581,646 A | 12/1996 | Tsukamoto et al. |
| 5,585,639 A | 12/1996 | Dorsel et al. |
| 5,600,744 A | 2/1997 | Takahashi |
| 5,614,386 A | 3/1997 | Metzker et al. |
| 5,621,031 A | 4/1997 | Leimann et al. |
| 5,623,561 A | 4/1997 | Hartman |
| 5,631,170 A | 5/1997 | Attridge |
| 5,635,608 A | 6/1997 | Haugland et al. |
| 5,640,234 A | 6/1997 | Roth et al. |
| 5,650,123 A | 7/1997 | Saini et al. |
| 5,671,303 A | 9/1997 | Shieh et al. |
| 5,677,196 A | 10/1997 | Herron et al. |
| 5,677,769 A | 10/1997 | Bendett |
| 5,710,000 A | 1/1998 | Sapolsky et al. |
| 5,712,937 A | 1/1998 | Asawa et al. |
| 5,728,529 A | 3/1998 | Metzker et al. |
| 5,734,768 A | 3/1998 | Kim et al. |
| 5,737,457 A | 4/1998 | Saini et al. |
| 5,800,992 A | 9/1998 | Fodor et al. |
| 5,814,565 A | 9/1998 | Reichert et al. |
| 5,822,472 A | 10/1998 | Danielzik et al. |
| 5,830,766 A | 11/1998 | Attridge et al. |
| 5,832,165 A | 11/1998 | Reichert et al. |
| 5,841,914 A | 11/1998 | Shieh et al. |
| 5,846,842 A | 12/1998 | Herron et al. |
| 5,861,242 A | 1/1999 | Chee et al. |
| 5,872,243 A | 2/1999 | Gee et al. |
| 5,919,712 A | 7/1999 | Herron et al. |
| 5,961,924 A | 10/1999 | Reichert et al. |
| 5,998,796 A | 12/1999 | Liu et al. |
| 6,027,880 A | 2/2000 | Cronin et al. |
| 6,040,403 A | 3/2000 | Starzewski |
| 6,057,466 A | 5/2000 | Starzewski |
| 6,108,463 A | 8/2000 | Herron et al. |
| 6,110,749 A | 8/2000 | Obremski et al. |
| 6,137,117 A | 10/2000 | Feldstein et al. |
| 6,141,465 A | 10/2000 | Bischel et al. |
| 6,191,852 B1 | 2/2001 | Paffhaen et al. |
| 6,222,619 B1 | 4/2001 | Herron et al. |
| 6,228,575 B1 | 5/2001 | Gingeras et al. |
| 6,239,876 B1 | 5/2001 | Brandenberg |
| 6,242,267 B1 | 6/2001 | Herron et al. |
| 6,287,871 B1 | 9/2001 | Herron et al. |
| 6,316,274 B1 | 11/2001 | Herron et al. |
| 6,335,793 B1 | 1/2002 | Freeman et al. |
| 6,340,598 B1 | 1/2002 | Herron et al. |
| 6,350,413 B1 | 2/2002 | Reichert et al. |
| 6,361,947 B1 | 3/2002 | Dong et al. |
| 6,384,912 B2 | 5/2002 | Kraus et al. |
| 6,389,186 B1 | 5/2002 | DiGiovanni et al. |
| 6,395,558 B1 | 5/2002 | Duveneck et al. |
| 6,396,995 B1 | 5/2002 | Stuelpnagel et al. |
| 6,437,345 B1 | 8/2002 | Bruno-Raimondi et al. |
| 6,465,241 B2 | 10/2002 | Haronian et al. |
| 6,469,785 B1 | 10/2002 | Duveneck et al. |
| 6,483,096 B1 | 11/2002 | Kunz et al. |
| 6,492,468 B1 | 12/2002 | Chen et al. |
| 6,498,041 B1 | 12/2002 | Tabacco et al. |
| 6,522,408 B1 | 2/2003 | Bruck et al. |
| 6,611,634 B2 | 8/2003 | Herron et al. |
| 6,618,536 B1 | 9/2003 | Heideman et al. |
| 6,632,609 B2 | 10/2003 | Lizardi |
| 6,661,938 B2 | 12/2003 | Lim et al. |
| 6,713,264 B2 | 3/2004 | Luttermann et al. |
| 6,759,663 B2 | 7/2004 | Tsipouras et al. |
| 6,777,244 B2 | 8/2004 | Pepper et al. |
| 6,785,432 B2 | 8/2004 | Letant et al. |
| 6,801,677 B1 | 10/2004 | Grace et al. |
| 6,830,936 B2 | 12/2004 | Anderson et al. |
| 6,847,746 B2 | 1/2005 | Uchiyama |
| 6,911,344 B1 | 6/2005 | Reichert et al. |
| 6,947,634 B2 | 9/2005 | Tanaka et al. |
| 6,951,715 B2 * | 10/2005 | Cunningham et al. ............ 435/4 |
| 6,956,651 B2 * | 10/2005 | Lackritz et al. ................ 356/445 |
| 6,961,490 B2 | 11/2005 | Maisenhoelder et al. |
| 6,974,673 B2 | 12/2005 | Lockhart |
| 6,979,567 B2 | 12/2005 | Herron et al. |
| 6,987,898 B2 | 1/2006 | Tran et al. |
| 7,046,893 B2 | 5/2006 | Dorn et al. |
| 7,057,031 B2 | 6/2006 | Olejnik et al. |
| 7,058,255 B1 | 6/2006 | Fang |
| 7,101,945 B2 | 9/2006 | Dorn et al. |
| 7,122,012 B2 | 10/2006 | Bouton et al. |
| 7,175,811 B2 | 2/2007 | Bach et al. |
| 7,203,386 B2 | 4/2007 | Krol et al. |
| 7,227,147 B2 | 6/2007 | Riehle et al. |
| RE39,772 E | 8/2007 | Herron et al. |
| 7,292,336 B2 | 11/2007 | Cunningham et al. |
| 7,308,166 B1 | 12/2007 | Peng et al. |
| 7,349,080 B2 | 3/2008 | Aklian |
| 7,358,079 B2 | 4/2008 | Schürmann-Mader et al. |
| 7,373,063 B2 | 5/2008 | Nakata et al. |
| 7,396,675 B2 | 7/2008 | Pawlak et al. |
| 7,410,784 B2 | 8/2008 | Hatch |
| 7,444,053 B2 | 10/2008 | Schmidt et al. |
| 7,447,391 B2 | 11/2008 | Peled et al. |
| 7,483,140 B1 | 1/2009 | Cho et al. |
| 7,545,494 B2 | 6/2009 | Haiml et al. |
| 7,627,201 B2 | 12/2009 | Tiefenthaler |
| 7,708,945 B1 | 5/2010 | Abel et al. |
| 7,811,754 B2 | 10/2010 | Herron et al. |
| 7,838,847 B2 | 11/2010 | Lundquist et al. |
| 7,879,598 B2 | 2/2011 | Zesch et al. |
| 7,922,976 B2 | 4/2011 | Dutta et al. |
| 8,187,866 B2 | 5/2012 | Duer |
| 2001/0001021 A1 | 5/2001 | Kraus et al. |
| 2002/0045811 A1 | 4/2002 | Kittrell et al. |
| 2002/0097947 A1 | 7/2002 | Lim et al. |
| 2002/0114576 A1 | 8/2002 | Schroeder |
| 2002/0126936 A1 | 9/2002 | Lockhart |
| 2002/0126938 A1 | 9/2002 | Lockhart |
| 2002/0172457 A1 | 11/2002 | Tapalian et al. |
| 2002/0191884 A1 | 12/2002 | Letant et al. |
| 2002/0197456 A1 | 12/2002 | Pope |
| 2003/0059853 A1 | 3/2003 | Lockhart |
| 2003/0063851 A1 | 4/2003 | Hillendahl et al. |
| 2003/0091277 A1 | 5/2003 | Mei |
| 2003/0108274 A1 | 6/2003 | Haronian |
| 2003/0108291 A1 | 6/2003 | Duveneck et al. |
| 2003/0138208 A1 | 7/2003 | Pawlak et al. |
| 2003/0169956 A1 | 9/2003 | Lange et al. |
| 2004/0008919 A1 | 1/2004 | Freeman et al. |
| 2004/0020987 A1 | 2/2004 | Nishioka et al. |
| 2004/0022475 A1 | 2/2004 | Pennington |
| 2004/0023396 A1 | 2/2004 | Boyd et al. |
| 2004/0036949 A1 | 2/2004 | Trezza |
| 2004/0046128 A1 | 3/2004 | Abel et al. |
| 2004/0052489 A1 | 3/2004 | Duveneck et al. |
| 2004/0081384 A1 * | 4/2004 | Datesman et al. ............... 385/12 |
| 2004/0142370 A1 | 7/2004 | Dosmann et al. |
| 2004/0197044 A1 | 10/2004 | Bloom |
| 2005/0018949 A1 | 1/2005 | Yan |
| 2005/0043139 A1 | 2/2005 | Kennedy |
| 2005/0078903 A1 | 4/2005 | Grace et al. |
| 2005/0088648 A1 | 4/2005 | Grace et al. |
| 2005/0089261 A1 | 4/2005 | Shimazaki |

| | | | |
|---|---|---|---|
| 2005/0110989 A1* | 5/2005 | Schermer et al. ............. 356/246 |
| 2005/0145783 A1 | 7/2005 | Zheng |
| 2005/0153320 A1 | 7/2005 | Herron et al. |
| 2005/0163659 A1 | 7/2005 | Duveneck et al. |
| 2005/0195394 A1 | 9/2005 | Ma et al. |
| 2005/0201657 A1 | 9/2005 | Tiefenthaler |
| 2005/0201659 A1 | 9/2005 | Strecker |
| 2005/0227231 A1 | 10/2005 | Tcherkassov |
| 2005/0254744 A1 | 11/2005 | Freeman |
| 2006/0008227 A1 | 1/2006 | Schmidt et al. |
| 2006/0014151 A1 | 1/2006 | Ogura et al. |
| 2006/0061754 A1 | 3/2006 | Turner et al. |
| 2006/0072873 A1 | 4/2006 | Tekippe et al. |
| 2006/0073491 A1 | 4/2006 | Joseph et al. |
| 2006/0078889 A1 | 4/2006 | Bhattacharjee et al. |
| 2006/0098927 A1 | 5/2006 | Schmidt et al. |
| 2006/0183145 A1 | 8/2006 | Turner |
| 2007/0077595 A1 | 4/2007 | Koo et al. |
| 2007/0211985 A1 | 9/2007 | Duer |
| 2007/0222704 A1 | 9/2007 | Huang |
| 2007/0231458 A1 | 10/2007 | Gale |
| 2007/0231880 A1 | 10/2007 | Chang-Yen |
| 2008/0117418 A1 | 5/2008 | Claps et al. |
| 2008/0243181 A1 | 10/2008 | Schneider et al. |
| 2009/0312188 A1 | 12/2009 | Duer et al. |
| 2010/0072396 A1 | 3/2010 | Agranat et al. |
| 2010/0167413 A1 | 7/2010 | Lundquist et al. |
| 2010/0202925 A1 | 8/2010 | Sonnleitner |
| 2010/0248352 A1 | 9/2010 | Song et al. |
| 2010/0256016 A1 | 10/2010 | Blair et al. |
| 2010/0279429 A1 | 11/2010 | Hildenbrand et al. |
| 2010/0302544 A1 | 12/2010 | Duer |

FOREIGN PATENT DOCUMENTS

| | | |
|---|---|---|
| EP | 0737308 B1 | 3/1998 |
| EP | 517516 B1 | 12/1999 |
| EP | 671626 B1 | 1/2000 |
| EP | 918984 B1 | 6/2001 |
| EP | 901620 B1 | 1/2002 |
| EP | 0783683 B1 | 4/2004 |
| EP | 1413876 A2 | 4/2004 |
| EP | 901623 B1 | 6/2004 |
| EP | 1441217 A2 | 7/2004 |
| EP | 1413876 A3 | 2/2005 |
| EP | 1441217 A3 | 7/2007 |
| EP | 1315968 B1 | 2/2008 |
| EP | 1635177 B1 | 7/2008 |
| EP | 2154128 B1 | 12/2010 |
| EP | 2144947 B1 | 3/2011 |
| EP | 1356291 B1 | 5/2011 |
| GB | 2377492 A | 1/2003 |
| WO | WO 92/21768 A1 | 12/1992 |
| WO | WO 94/18544 A1 | 8/1994 |
| WO | WO 94/27137 A2 | 11/1994 |
| WO | WO 94/28395 A1 | 12/1994 |
| WO | WO 95/14225 A1 | 5/1995 |
| WO | WO 95/33197 A1 | 12/1995 |
| WO | WO 95/33198 A1 | 12/1995 |
| WO | WO 96/26432 A1 | 8/1996 |
| WO | WO97/35176 A1 | 9/1997 |
| WO | WO 97/35181 A1 | 9/1997 |
| WO | WO 97/35203 A1 | 9/1997 |
| WO | WO 97/39370 A1 | 10/1997 |
| WO | WO 99/14594 A1 | 3/1999 |
| WO | WO 99/45354 A2 | 9/1999 |
| WO | WO 99/45354 A3 | 10/1999 |
| WO | WO 00/75644 A1 | 12/2000 |
| WO | WO01/55691 A2 | 8/2001 |
| WO | WO02/37148 A2 | 5/2002 |
| WO | WO02/40998 A2 | 5/2002 |
| WO | WO 02/46756 A1 | 6/2002 |
| WO | WO 02/066983 A2 | 8/2002 |
| WO | WO 03/006625 A2 | 1/2003 |
| WO | WO03/021253 A2 | 3/2003 |
| WO | WO 02/066983 A3 | 5/2003 |
| WO | WO 03/062791 A2 | 7/2003 |
| WO | WO 03/062791 A3 | 7/2003 |
| WO | WO 2004/020987 A1 | 3/2004 |
| WO | WO2004/023142 A1 | 3/2004 |
| WO | WO2004/023143 A2 | 3/2004 |
| WO | WO 2005/043139 A1 | 5/2005 |
| WO | WO 2005/084367 A2 | 9/2005 |
| WO | WO 2006/135782 A2 | 12/2006 |
| WO | WO 2007/070869 A2 | 6/2007 |
| WO | WO 2007/094817 A2 | 8/2007 |
| WO | WO 2008/069973 A2 | 6/2008 |

OTHER PUBLICATIONS

Ausubel, et al. (Eds.), Short Protocols in Molecular Biology: A Compendium of Methods from Current Protocols in Molecular Biology, 5th Ed., John Wiley & Sons, Inc. (2002).

Batzer, et al. Enhanced evolutionary PCR using oligonucleotides with inosine at the 3'-terminus. Nucleic Acid Res. 1991; 19:5081.

Bieche, et al. Quantitation of MYC gene expression in sporadic breast tumors with a real-time reverse transcription-PCR assay. Cancer Res. Jun. 15, 1999;59(12):2759-65.

Chee, et al. Accessing genetic information with high density DNA arrays. Science. 1996; 274:610-614.

Herron, et al. Orientation and Activity of Immobilized Antibodies. In: Biopolymers at Interfaces, 2nd Edition (M. Malmsten, ed.). Surfactant Science Series. Marcel Dekker, New York. 2003; 110:115-163.

Herron, et al. Planar waveguide biosensors for point-of-care clinical and molecular diagnostics. In: Fluorescence Sensors and Biosensors. R. B. Thompson, Ed. CRC Press Taylor & Francis Group. Boca Raton, FL. 2005: 283-332.

Innis, et al. (Eds.) PCR Protocols: A Guide to Methods and Applications, Elsevier Science & Technology Books (1990).

Kreuzer, et al. LightCycler technology for the quantitation of bcr/abl fusion transcripts. Cancer Research. 1999; 59(13):3171-4.

Laurendeau, et al. Quantitation of MYC gene expression in sporadic breast tumors with a real-time reverse transcription-PCR assay. Clin Chem. 1999; 59(12):2759-65.

Laurendeau, et al. TaqMan PCR-based gene dosage assay for predictive testing in individuals from a cancer family with INK4 locus haploinsufficiency. Clin Chem. 1999; 45(7):982-6.

Ohtsuka, et al. An alternative approach to deoxyoligonucleotides as hybridization probes by insertion of deoxyinosine at ambiguous codon positions. J. Biol. Chem. 1985; 260:2605-2608.

Rossolini, et al. Use of deoxyinosine-containing primers vs degenerate primers for polymerase chain reaction based on ambiguous sequence information. Mol. Cell. Probes. 1994; 8:91-98.

Saizieu, et al. Bacterial transcript imaging by hybridization of total RNA to oligonucleotide arrays. Nat Biotechnol. 1998; 16(1):45-8.

Sambrook, et al., Molecular Cloning: A Laboratory Manual, 3rd Ed., Cold Spring Harbor Laboratory Press (2000).

Burgess et al.; A New Photolabile Protecting Group for Nucleotides; Abstracts of Papers Part 2.; 211th ACS National Meeting, American Chemical Society; New Orleans, LA; Mar. 24-28, 1996.

Hutchison, Clyde A.; DNA sequencing: bench to bedside and beyond; Nucleic Acid Res.; vol. 35; No. 18; pp. 6227-6237; Sep. 2007.

Kaplan et al.;Rapid photolytic release of adenosine 5'-triphosphate from a protected analog: utilization by the sodium:potassium pump of human red blood ghost cells; Biochemistry; vol. 17; pp. 1929-1935; May 1978.

Kulagina et al.; Antimicrobial peptides as new recognition molecules for screening challenging species; (Author Manuscript) Sens. Actuators B. chem.; vol. 121 (1); pp. 150-157; Jan. 2007.

Lockhart et al.; Expression monitoring by hybridization to high-density oligonucleotide arrays; Nature Biotechnology; vol. 14; pp. 1675-1680; Dec. 1996.

McCray et al.; A new approach to time-resolved studies of ATP-requiring biological systems; laser flash photolysis of caged ATP; Proc. Natl. Acad. Sci. USA; vol. 77; No. 12; pp. 7237-7241; Dec. 1980.

Metzker et al.; Termination of DNA synthesis by novel 3'-modified-deoxyribonucleoside 5'-triphosphates; Nucleic Acids Res.; vol. 22; No. 20; pp. 4259-4267; Oct. 1994.

Pillai, Rajasekharan V.N.; V.N.; Photoremovable Protecting Groups in Organic Synthesis ; Synthesis; 1980(1); pp. 1-26; Jan. 1980.

Plowman et al.; Femtomolar Sensitivity using a channel-etched Thin Film Waveguide Fluoroimmunosensor; Biosensors & Bioelectronics; vol. 11(1-2); pp. 149-160; Jan. 1996.

Sun et al.; Synthesis of Novel Flourinated Coumarins: Excellent UV-Light Excitable Flourencent Dyes: Bioorganic & Med. Letters; vol. 8; No. 22; pp. 3107-3110; Nov. 1998.

Xu et al.; Protein and chemical microarrays—powerful tools for proteomics; J Biomed Biotechnol; vol. 2003(5); pp. 257-266; Dec. 2003.

Zehavi et al.; J. Light-sensitive glycosides. I. 6-nytroveratryl .beta.-D-glucopyranoside and 2-nitrobenzyl beta.-D-glucopyranoside; J. Organic Chem.; vol. 37(14); pp. 2281-2285; Jul. 1972.

Zourob et al.; Principles of bacterial detection: Biosensors, Recognition Receptors and microsystems; Eds., Springer Science and Business Media, NY; pp. 178-180; Jun. 2008.

* cited by examiner

WAVEGUIDE-BASED OPTICAL SCANNING SYSTEMS

CROSS-REFERENCE

This application claims the benefit of U.S. Provisional Application No. 60/971,878, filed Sep. 12, 2007, which application is incorporated herein by reference.

BACKGROUND OF THE INVENTION

Biological substance analysis methods based on optical means have risen in popularity in the last couple of decades. Common to all these methods is that chemical interactions between the bio-molecules produce changes that affect some measurable optical properties, such as emission spectrum, absorption spectrum and index of refraction. The changes in the optical properties can occur in the analyte itself or through a mediator such as the surface on which the interaction takes place. These changes are then monitored using a beam of incoming light (usually laser light) which in-turn changes the outgoing light spectrum (e.g. in fluorescence), intensity (e.g. in absorption), or phase (e.g. Surface Plasmon Resonance=SPR and any kind of interferometric method).

While most of these optical bio-analysis methods have found niche applications and markets, one method that became highly popular and influential was microarray optical fluorescence scanning. Such optical scanning has enabled running tests on tens of thousands of miniature samples in a relatively short period of time. The major advantages of this method include: a) performance (sensitivity and Signal to Noise Ratio=SNR); b) speed; and c) miniaturization of the sampled analyte. These parameters define the efficiency and superiority of the method.

Currently microarray elements are spotted on top of a flat substrate chip usually made of glass, plastic or epoxy. Subsequently, the chip is scanned using confocal scanning systems where the exciting light and the resulting fluorescence light are both shined and collected from above and analyzed using a single photo-multiplier (PMT) detector. This arrangement suffers from several inherent limitations including a very short interaction length between the bio-sample and the light (usually a single mono-layer). This limits the signal strength and thus the SNR. Another limitation is a high background or noise due to the fact that the back reflected light and the emitted fluorescent light travel in the same direction. A further limitation is high sensitivity to the planarity and the position of the chip that need to be maintained in focus. Still another limitation is slow operation due to the need to have large enough number of 'pixels' (scanned spots) within every sample and long enough integration time. Yet another limitation is the need for a complicated optical and mechanical structure that entails bulky and expensive systems.

Another optical bio-analysis method is waveguide based bio-sensors. Bio-sensing based on waveguides has been around for a while. These biosensors can be divided into three main categories. The first involve slab waveguide fluorescence excitation with light collection from above or below the chip. In this arrangement the bio-analyzed spots are located on the surface of a chip that contains a single slab-waveguide. Light is coupled into the waveguide using a lens or a grating that excites the entire chip with all its bio-analyzed spots simultaneously. The fluorescence is collected using an optical imaging system and a Charge-Coupled Device (CCD) detector from above or underneath the chip. One drawback of this kind of systems is relatively poor performance due to uniformity of excitation as well as collection of the light. This leads to non-repeatable results. Another drawback is high noise levels due to crosstalk between the different spots. A further drawback is that large spots and relatively small numbers of elements are required to generate signal large enough for efficient imaging with the CCD. Yet another drawback is the long integration time to overcome SNR issues. Examples of the above method are described in U.S. Pat. Nos. 5,814,565; 6,911,344 and 6,395,558.

A second waveguide based bio-sensor utilizes an interferometric optical device. In this case, channel waveguides are used together with interferometric devices such as Mach Zehnder Interferometers (MZI) or ring-resonators. These sensitive interferometric devices sense the change in the index of refraction due to binding of the bio-molecules near a waveguide surface. The major problems associated with this type of systems include non-specificity due to inability to recognize the exact reason for the index change which may occur from other material deposition as well as temperature changes. Another problem is a very slow speed in addressing the different elements which disqualify this method for running large numbers of element arrays. Examples of the above method are described in U.S. Pat. Nos. 5,494,798 4,515,430, 5,623,561 and 6,618,536.

A third waveguide based bio-sensor utilizes Surface Plasmon Resonance (SPR). Here, in one example, a thin gold layer deposited on top of a glass substrate. The bio-analyzed sample on top of the gold induces changes in the refractive index above the gold layer and thus changing the resonant angle for generating surface Plasmons along the gold layer. The Plasmons generation is detected as an enhanced peak in the reflected beam. Examples of the SPR method are covered, for example, in U.S. Pat. No. 6,956,651 B2. Other types of optical bio-sensors and array scanners exist such as described in U.S. Pat. No. 6,396,995 B1.

SUMMARY OF THE INVENTION

In general, in one aspect, the invention features a scanning sensor system, methods and kits for use thereof including a light source, a detector, a substrate and a plurality of optical sensing sites. The substrate is in optical communication with the light source and the detector either directly or indirectly, for example, through an adapter chip. Additionally, the substrate includes a plurality of substantially parallel waveguides used both for guiding the excitation light to the sensing sites and for collecting the emitted light from the sensing sites. The plurality of optical sensing sites can each be in optical communication with a waveguide.

Implementations of the invention can include one or more of the following features.

In general in one aspect a scanning sensor system for detecting a biologically active analyte is provided including a light source, a detector, a substrate comprising a plurality of waveguides and a plurality of optical sensing sites in optical communication with one or more waveguide of the substrate, and at least one adapter configured to couple with the substrate and provide optical communication between the light source, the waveguides of the substrate, and the detector.

The substrate and the at least one adapter in some embodiments can be substantially planar and make up or comprise a planar lightwave circuit. The at least one adapter can be further configured to removably couple with the substrate. The at least one adapter can be further coupled to at least one of the light source and the detector. The at least one adapter can in one embodiment be a single adapter further coupled to the light source and the detector.

Coupling of the system components can be by fiber optic.

The adapter in some embodiments includes a plurality of edges and coupling of the adapter to the light source and the detector includes coupling to a first edge of the adapter and coupling to the substrate comprises coupling at a second edge of the adapter.

The plurality of waveguides of the substrate and/or the adapter can include in-coupling waveguides and out-coupling waveguides. The in-coupling waveguides can be coupled to the out-coupling waveguides through a combiner. In one embodiment the substrate further includes at least one combiner. In another embodiment the adapter further includes at least one combiner.

In a particular embodiment the at least one adapter is a single adapter, the plurality of waveguides include in-coupling waveguides and out-coupling waveguides, wherein the in-coupling waveguides are coupled to the out-coupling waveguides through a combiner, wherein the light source comprises a light generator element coupled to at least one in-coupling waveguide, and wherein the detector includes a detector element coupled to at least one out-coupling waveguide.

The optical sensing site can include a sensor configured to transduce a first light wave generated by the light source in a waveguide, resulting in a second light wave in the same waveguide, the second light wave being detectable by the detector.

The plurality of waveguides can be in-coupling waveguides coupled to out-coupling waveguides by way of combiners, and a first light wave can be carried by an in-coupling waveguide and a second light wave can be carried by an out-coupling waveguide. In one embodiment the adapter and substrate include inter-coupling optically communicating in-coupling waveguides and out-coupling waveguides and the substrate further includes the combiners.

The sensor can include a biologically active analyte in a sample, and wherein a measurable change in a first light wave results when the sensor discriminates or interacts with the biologically active analyte. In one embodiment the sensor is adapted to support an immunoassay. The immunoassay supported can be an enzyme-linked immunosorbent assay (ELISA). The immunoassay supported can be a fluorescent immunoassay.

The sensor can be selected from the group including a fluorescence well, an absorption cell, an interferometric sensor, a diffractive sensor and surface plasmon resonance sensor.

The biologically active analyte can be selected from the group including a nucleic acid, a protein, an antigen, an antibody, a microorganism, a gas, a chemical agent and a pollutant. In one embodiment the nucleic acid is produced via an amplification reaction.

The waveguides can be single-mode. The waveguides can alternatively be multi-mode. In one embodiment the waveguides are single-mode in the vertical dimension and multi-mode in the lateral dimension.

The optical sensing sites can include wells. In one embodiment the optical sensing sites include the surface of the substrate above the waveguides, In another embodiment the optical sensing sites include biochemical interaction sites. In a further embodiment the optical sensing sites include optical transducers. The optical transducers can include fluorescence wells comprising fluorescent or luminescent compounds, wherein light waves guided by a waveguide of the plurality of waveguides excite the fluorescent or luminescent compound in the wells in the presence of a biologically active analyte, and the same waveguide collects and guides light emitted from the wells to the detector.

The number of optical sensing sites can be greater than 10, greater than 200, or greater than 5,000.

The light source can be switchable or passive. In one embodiment the light source includes a dynamic light source. In one embodiment the light source is a passive 1×N splitter with N being between 1 and 1000.

The light source can include a chip containing an array of light generators coupled to an array of waveguides. In one embodiment the light source is an optical switch including a light generator coupled to one or more input of the optical switch. In another embodiment the optical switch further includes a branched architecture. The optical switch can further include one or more inputs and multiple outputs. The optical switch can further include greater than about 10 outputs, greater than about 100 outputs or greater than about 1,000 outputs. In one embodiment the optical switch further includes substantially between 20 and 200 outputs.

The light generator can provide variable wavelengths of light. The light generator can be selected from the group including a broad-band source, a source with one or more discrete spectral lines and a tunable source.

The light source can be butt-coupled to one or more of the at least one adapter. In one embodiment the light source includes one or more waveguide and is evanescently coupled to the at least one adapter through a proximate arrangement of the one or more light source waveguide and one or more waveguide of the at least one adapter.

The detector can be a photodetector array. In one embodiment the detector is a plurality of detectors. In another embodiment two or more detectors are coupled to and in optical communication with one or more waveguide of the at least one adapter at one or more edges of the at least one adapter.

The system can further include a thermal transfer element in thermal communication with the substrate. In one embodiment the thermal transfer element is a thermoelectric cooler. In another embodiment each optical sensing site includes a thermal transfer element in thermal communication with the optical sensing site. The thermal transfer element can include a thin-film heater. In one embodiment each optical sensing site further includes a thermistor in thermal communication with the optical sensing site.

The substrate can further include one or more microchannel and one or more reservoirs in fluid communication with one or more optical sensing site. In one embodiment the system further includes a fluidics layer coupled to the substrate and includes one or more microchannel and one or more reservoirs in fluid communication with one or more optical sensing site.

In general in another aspect a scanning sensing method is provided including coupling a removable substrate including a plurality of in-coupling waveguides, a plurality of out-coupling waveguides and combiners for coupling the in-coupling and out-coupling waveguides, wherein the substrate is coupled in optical communication with an adapter, a light source, and a detector to provide a scanning sensor system, wherein the adapter is coupled to the light source and the detector. The method further includes delivering a sample suspected of containing a biologically active analyte to be detected to an optical sensing site of the substrate, providing a first light wave using a light source to one or more of the plurality of in-coupling waveguides of the substrate, wherein the in-coupling waveguides are in optical communication with the optical sensing site, wherein the first light wave is transducable by a sensor associated with the optical sensing site to a second light wave carried to an out-coupling waveguide, and detecting a measurable change in the second light wave using the detector, wherein a measurable change in the first light waves occurs when the sensor interacts with the biologically active analyte.

Scanning sensing can further include switching one or more input light wave from the light source into the substrate to produce the first light wave in one or more of the in-coupling waveguides. In one embodiment the light source includes an optical switch for controlled switching of one or more input light wave, the optical switch can multicast light to a plurality of outputs and into the substrate to controllably produce the first light wave in one or more of the in-coupling waveguides. The light source can include an array of individually controlled light generators for controlled switching of one or more input light wave, to controllably produce the first light wave in one or more of the in-coupling waveguides.

The method can further include simultaneously detecting the second light wave with the detector wherein the detector comprises a photodetector array.

In one embodiment a portion of the sensing sites include reference sample material for calibration and/or normalization.

The biologically active analyte can be selected from the group consisting of a nucleic acid, a protein, an antigen, an antibody, a microorganism, a gas, a chemical agent and a pollutant. In one embodiment the biologically active analyte is a protein. In another embodiment a single nucleotide polymorphism (SNP) is detected in the biologically active analyte. In a further embodiment expression of a gene is detected upon detection of the biologically active analyte.

The sensor can be adapted to support an immunoassay and wherein the sensor interacting with the biologically active analyte includes an outcome of an immunoassay. In one embodiment the immunoassay supported is an enzyme-linked immunosorbent assay (ELISA). The immunoassay supported can be a fluorescent immunoassay.

Detecting a measurable change in the second lightwave can provide a diagnostic result.

The method can further include conducting a real-time PCR reaction at the optical sensing site.

In general in another aspect a kit for assaying a sample for a biologically active analyte is provided including a scanning sensor system including a light source, a detector, a substrate comprising a plurality of waveguides and a plurality of optical sensing sites in optical communication with one or more waveguide of the substrate, and at least one adapter configured to couple with the substrate and provide optical communication between the light source, the waveguides of the substrate, and the detector. The kit further includes packaging and instructions for use of the system. In one embodiment the adapter and substrate includes a planar lightwave circuit. In another embodiment the optical sensing sites includes a sensor adapted to support an immunoassay, and wherein the kit further includes one or more immunoassay reagents.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present methods and compositions may be obtained by reference to the following detailed description that sets forth illustrative embodiments, in which the principles of our methods, compositions, devices and apparatuses are utilized, and the accompanying drawings of which:

DETAILED DESCRIPTION OF THE INVENTION

Figure 1A:
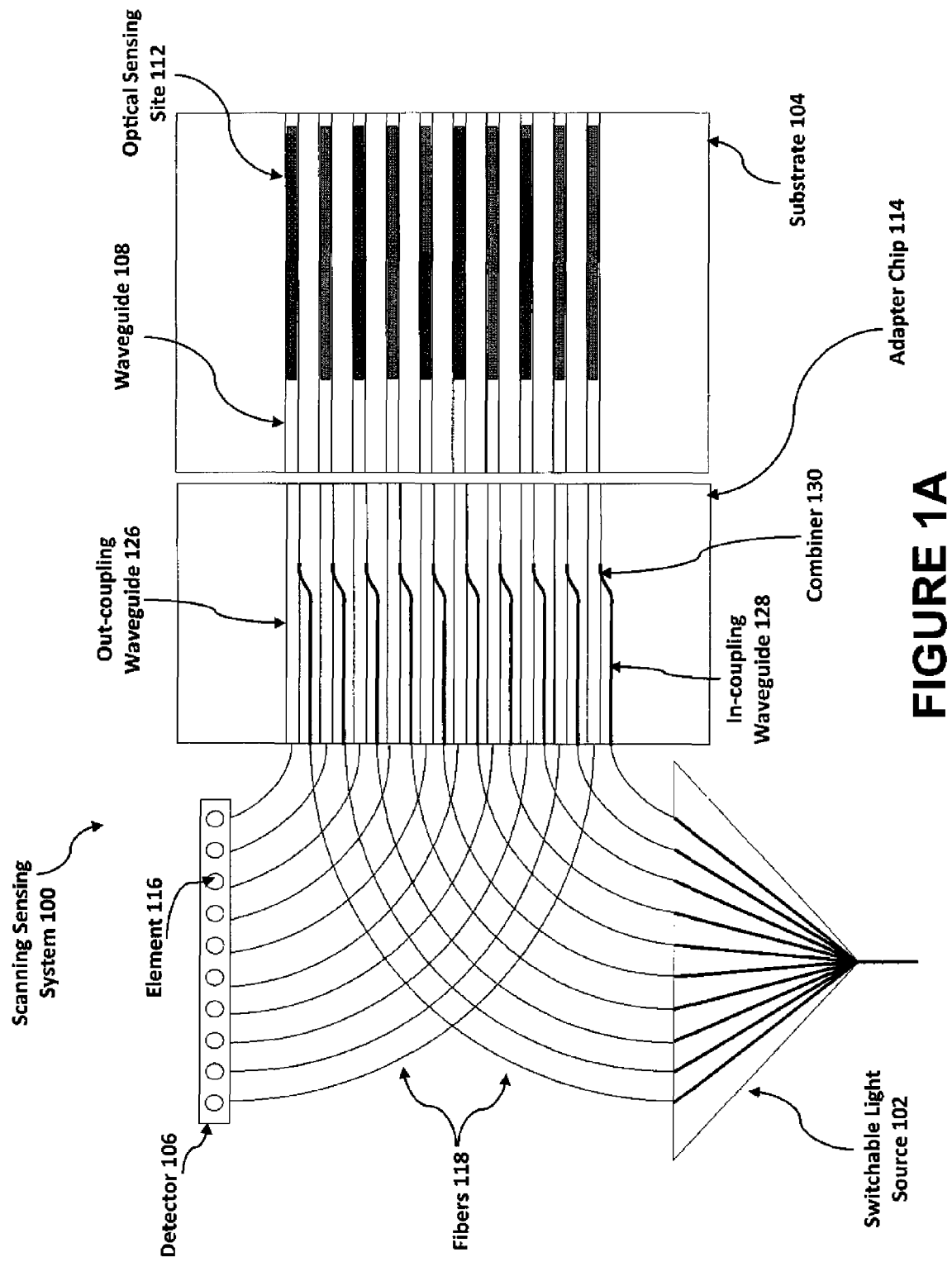
FIG. 1A is a schematic of the scanning sensing system according to one embodiment of the invention including a switchable light source, fibers, an adapter chip, a substrate, optical sensing sites and a detector.

Apparatus, methods, and kits for optical sensing, using a scanning sensing system including a light source, a detector, at least one adapter, a substrate and a plurality of optical sensing sites are provided. Related scanning sensing systems, methods and kits including such systems have been previously described in U.S. patent application Ser. No. 11/683,808 filed Mar. 8, 2007, the entire contents of which are incorporated herein by reference. The substrate of the present system includes a plurality of substantially parallel waveguides and a plurality of sensing sites. Advantageously the at least one adapter of the system can provide for removable coupling of the substrate with system components. The optical sensing sites include a sensor and are in optical communication with one or more waveguides. Sensing of a variety of environmental and biological samples can be achieved using the apparatus, methods and kits described herein. The general theoretical principles of lightwave guiding and evanescent field fluorescence excitation apply to the embodiments disclosed herein.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

A biologically active analyte can be any substance which can affect any physical or biochemical properties of a biological organism, including but not limited to viruses, bacteria, fungi, plants, animals, and humans. In particular as used herein, biologically active analyte according to the present invention includes without limitation drugs, prodrugs, pharmaceutical agents, drug metabolites, biomarkers such as expressed proteins and cell markers, antibodies, serum proteins, cholesterol, polysaccharides, nucleic acids, biological analytes, gene, protein, or hormone, or any combination thereof. A biologically active analyte can further include a natural or man-made substance including but not limited to a gas, a chemical agent or a pollutant, or a combination thereof (e.g., from an environmental source). At a molecular level, the biologically active analytes can be polypeptide glycoprotein, polysaccharide, lipid, nucleic acid, and a combination thereof.

Of particular interest are biomarkers associated with a particular disease or with a specific disease stage.

Such biologically active analytes include but are not limited to those associated with autoimmune diseases, obesity, hypertension, diabetes, neuronal and/or muscular degenerative diseases, cardiac diseases, endocrine disorders, any combinations thereof.

Also of interest are biomarkers that are present in varying abundance in one or more of the body tissues including heart, liver, prostate, lung, kidney, bone marrow, blood, skin, bladder, brain, muscles, nerves, and selected tissues that are affected by various disease, such as different types of cancer (malignant or non-metastatic), autoimmune diseases, inflammatory or degenerative diseases.

Also of interest are biologically active analytes that are indicative of a microorganism. Exemplary microorganisms include but are not limited to bacterium virus, fungus and protozoa. Biologically active analytes that can be detected by the subject method also include blood-born pathogens selected from a non-limiting group that consists of *Staphylococcus epidermidis, Escherichia coli*, methicillin-resistant *Staphylococcus aureus* (MSRA),

*Staphylococcus aureus, Staphylococcus hominis, Enterococcus faecalis, Pseudomonas aeruginosa, Staphylococcus capitis, Staphylococcus warneri, Klebsiella pneumoniae, Haemophilus influnzae, Staphylococcus simulans, Streptococcus pneumoniae* and *Candida albicans*.

Biologically active analytes that can be detected by the subject device and methods also encompass a variety of sexually transmitted diseases selected from the following: gonorrhea (*Neisseria gorrhoeae*), syphilis (*Treponema pallidum*), chlamydia (*Chlamydia tracomitis*), nongonococcal urethritis (*Ureaplasma urealyticum*), yeast infection (*Candida albicans*), chancroid (*Haemophilus ducreyi*), trichomoniasis (*Trichomonas vaginalis*), genital herpes (HSV type I and II), HIV I, HIV II and hepatitis A, B, C, G, as well as hepatitis caused by TTV.

Additional biologically active analytes that can be detected by the subject apparatus and methods encompass a diversity of respiratory pathogens including but not limited to *Pseudomonas aeruginosa*, methicillin-resistant

*Staphylococcus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis,*

*Streptococcus pneumoniae, Citrobacter freundii, Enterococcus faeciurn, Klebsiella oxytoca, Pseudomonas fluorsecens, Neisseria meningitidis, Streptococcus pyogenes, Pneumocystis carinii, Klebsiella pneumoniae, Legionella pneumophila, Mycoplasma pneumoniae,* and *Mycobacterium tuberculosis.*

Listed below are additional exemplary markers according to the present invention: Theophylline, CRP, CKMB, PSA, Myoglobin, CA125, Progesterone, TxB2, 6-keto-PGF-1-alpha, and Theophylline, Estradiol, Lutenizing hormone, High sensitivity CRP, Triglycerides, Tryptase, Low density lipoprotein Cholesterol, High density lipoprotein Cholesterol, Cholesterol, IGFR.

Exemplary liver markers include without limitation LDH, (LD5), (ALT), Arginase 1 (liver type), Alphafetoprotein (AFP), Alkaline phosphatase, Alanine aminotransferase, Lactate dehydrogenase, and Bilirubin.

Exemplary kidney markers include without limitation TNFa Receptor, Cystatin C, Lipocalin-type urinary prostaglandin D, synthatase (LPGDS), Hepatocyte growth factor receptor, Polycystin 2, Polycystin 1, Fibrocystin, Uromodulin, Alanine, aminopeptidase, N-acetyl-B-D-glucosaminidase, Albumin, and Retinol-binding protein (RBP).

Exemplary heart markers include without limitation Troponin I (TnI), Troponin T (TnT), CK, CKMB, Myoglobin, Fatty acid binding protein (FABP), CRP, D-dimer, S-100 protein, BNP, NT-proBNP, PAPP-A, Myeloperoxidase (MPO), Glycogen phosphorylase isoenzyme BB (GPBB), Thrombin Activatable Fibrinolysis Inhibitor (TAFI), Fibrinogen, Ischemia modified albumin (IMA), Cardiotrophin-1, and MLC-I (Myosin Light Chain-I).

Exemplary pancreas markers include without limitation Amylase, Pancreatitis-Associated protein (PAP-1), and Regeneratein proteins (REG).

Exemplary muscle tissue markers include without limitation Myostatin.

Exemplary blood markers include without limitation Erythopoeitin (EPO).

Exemplary bone markers include without limitation, Cross-linked N-telopeptides of bone type I collagen (NTx), Carboxyterminal cross-linking telopeptide of bone collagen, Lysyl-pyridinoline (deoxypyridinoline), Pyridinoline, Tartrate-resistant acid phosphatase, Procollagen type I C propeptide, Procollagen type I N propeptide, Osteocalcin (bone glaprotein), Alkaline phosphatase, Cathepsin K, COMP (Cartilage Oligomeric Matrix Protein), Osteocrin, Osteoprotegerin (OPG), RANKL, sRANK, TRAP 5 (TRACP 5), Osteoblast Specific Factor 1 (OSF-1, Pleiotrophin), Soluble cell adhesion molecules, sTfR, sCD4, sCD8, sCD44, and Osteoblast Specific Factor 2 (OSF 2, Periostin).

In some embodiments markers according to the present invention are disease specific. Exemplary cancer markers include without limitation PSA (total prostate specific antigen), Creatinine, Prostatic acid phosphatase, PSA complexes, Prostrate-specific gene-1, CA 12-5, Carcinoembryonic Antigen (CEA), Alpha feto protein (AFP), hCG (Human chorionic gonadotropin), Inhibin, CAA Ovarian C1824, CA 27.29, CA 15-3, CAA Breast C1924, Her-2, Pancreatic, CA 19-9, Carcinoembryonic Antigen, CAA pancreatic, Neuron-specific enolase, Angiostatin, DcR3 (Soluble decoy receptor 3), Endostatin, Ep-CAM (MK-1), Free Immunoglobulin Light Chain Kappa, Free Immunoglobulin Light Chain Lambda, Herstatin, Chromogranin A, Adrenomedullin, Integrin, Epidermal growth factor receptor, Epidermal growth factor receptor-Tyrosine kinase, Pro-adrenomedullin N-terminal 20 peptide, Vascular endothelial growth factor, Vascular endothelial growth factor receptor, Stem cell factor receptor, c kit/KDR, KDR, and Midkine.

Exemplary infectious disease markers include without limitation Viremia, Bacteremia, Sepsis, PMN Elastase, PMN elastase/α1-PI complex, Surfactant Protein D (SP-D), HBVc antigen, HBVs antigen, Anti-HBVc, Anti-HIV, Tsuppressor cell antigen, T-cell antigen ratio, T-helper cell antigen, Anti-HCV, Pyrogens, p24 antigen, Muramyldipeptide.

Exemplary diabetes markers include without limitation C-Peptide, Hemoglobin A1c, Glycated albumin, Advanced glycosylation end products (AGEs), 1,5-anhydroglucitol, Gastric Inhibitory Polypeptide, Glucose, Hemoglobin, ANGPTL3 and 4.

Exemplary inflammation markers include without limitation Rheumatoid factor (RF), Antinuclear Antibody (ANA), C-reactive protein (CRP), Clara Cell Protein (Uteroglobin).

Exemplary allergy markers include without limitation Total IgE and Specific IgE.

Exemplary autism markers include without limitation Ceruloplasmin, Metalothioneine, Zinc, Copper, B6, B12, Glutathione, Alkaline phosphatase, and Activation of apo-alkaline phosphatase.

Exemplary coagulation disorders markers include without limitation b-Thromboglobulin, Platelet factor 4, Von Willebrand factor.

In some embodiments a marker may be therapy specific. COX inhibitors include without limitation TxB2 (Cox-1), 6-keto-PGF-1-alpha (Cox 2), 11-Dehydro-TxB-1a (Cox-1).

Other markers of the present include without limitation Leptin, Leptin receptor, and Procalcitonin, Brain S100 protein, Substance P, 8-Iso-PGF-2a.

Exemplary geriatric markers include without limitation, Neuron-specific enolase, GFAP, and S100B.

Exemplary markers of nutritional status include without limitation Prealbumin, Albumin, Retinol-binding protein (RBP), Transferrin, Acylation-Stimulating Protein (ASP), Adiponectin, Agouti-Related Protein (AgRP), Angiopoietin-like Protein 4 (ANGPTL4, FIAF), C-peptide, AFABP (Adipocyte Fatty Acid Binding Protein, FABP4), Acylation-Stimulating Protein (ASP), EFABP (Epidermal Fatty Acid Binding Protein, FABP5), Glicentin, Glucagon, Glucagon-Like Peptide-1, Glucagon-Like Peptide-2, Ghrelin, Insulin, Leptin, Leptin Receptor, PYY, RELMs, Resistin, and sTfR (soluble Transferrin Receptor).

Exemplary markers of Lipid metabolism include without limitation Apo-lipoproteins (several), Apo-A1, Apo-B, Apo-C-CII, Apo-D, Apo-E.

Exemplary coagulation status markers include without limitation Factor I: Fibrinogen, Factor II: Prothrombin, Factor III: Tissue factor, Factor IV: Calcium, Factor V: Proaccelerin, Factor VI, Factor VII: Proconvertin, Factor VIII: Antihemolytic factor, Factor IX: Christmas factor, Factor X: Stuart-Prower factor, Factor XI: Plasma thromboplastin antecedent, Factor XII: Hageman factor, Factor XIII: Fibrin-stabilizing factor, Prekallikrein, High molecular-weight kininogen, Protein C, Protein S, D-dimer, Tissue plasminogen activator, Plasminogen, a2 Antiplasmin, Plasminogen activator inhibitor 1 (PAI1).

Exemplary monoclonal antibody markers include those for EGFR, ErbB2, and IGF1R.

Exemplary tyrosine kinase inhibitor markers include without limitation Ab1, Kit, PDGFR, Src, ErbB2, ErbB 4, EGFR, EphB, VEGFR1-4, PDGFRb, FLt3, FGFR, PKC, Met, Tie2, RAF, and TrkA.

Exemplary Serine/Threonine Kinase Inhibitor markers include without limitation AKT, Aurora A/BIB, CDK, CDK (pan), CDK1-2, VEGFR2, PDGFRb, CDK4/6, MEK1-2, mTOR, and PKC-beta.

GPCR target markers include without limitation Histamine Receptors, Serotonin Receptors, Angiotensin Receptors, Adrenoreceptors, Muscarinic Acetylcholine Receptors, GnRH Receptors, Dopamine Receptors, Prostaglandin Receptors, and ADP Receptors.

A therapeutic agent can be any substances that have therapeutic utility and/or potential. Such substances include but are not limited to biological or chemical compounds such as a simple or complex organic or inorganic molecules, peptides, proteins (e.g. antibodies) or a polynucleotides (e.g. anti-sense). Other therapeutic agents include a vast array of compounds that can be synthesized, for example, polymers, such as polypeptides and polynucleotides, and synthetic organic compounds based on various core structures. In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters rapidly from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the PD parameters fall outside the desired range during a treatment regime, immediate action may have to be taken as well.

In preferred embodiments physical parameter data is stored in or compared to stored profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more patients to enter clinical trials in a safe fashion earlier than currently allowed. In another embodiment biomarkers discovered in human tissue studies can be targeted by the scanning sensing system for improved accuracy in determining drug pathways and efficacy in cancer studies.

A nucleic acid can be deoxyribonucleotides, deoxyribonucleosides, ribonucleosides or ribonucleotides and polymers thereof in either single- or double-stranded form. Nucleic acids may contain known analogues of natural nucleotides which have similar binding properties as the reference nucleic acid and are metabolized in a manner similar to naturally occurring nucleotides. Nucleic acids may also include oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

Microorganism can include but is not limited to bacteria, actinomycetales, cyanobacteria (unicellular algae), fingi, protozoa, animal cells or plant cells or virus. Examples of microorganisms include but are not limited to pathogens.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins (i.e., antigens), wherein the amino acid residues are linked by covalent peptide bonds. In addition, proteins that contain multiple polypeptide chains that associate through covalent and/or non-covalent interactions are also encompassed by "protein," as used herein.

A polymorphism is the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A dialelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

An individual includes but is not limited to a human being, but may also include other organisms including but not limited to mammals, plants, bacteria or cells derived from any of the above.

Aspects of the invention may include one or more of the following advantageous features. Dense and accurate integration of optical manipulating elements can be achieved using planar lightwave circuits technology. Applications for planar lightwave circuits as described herein include new drag discovery and development, disease research, biomarkers discovery, SNP association studies including toxicology and disease susceptibility, and diagnostics including identifying patients predisposed to diseases and identifying patients with particular drug sensitivity.

FIG. 1A illustrates an exemplary scanning sensing system 100 of the invention including a switchable light source 102, an adapter chip 114, a substrate 104, optical sensing sites 112 and a detector 106. Although a switchable light source is illustrated in the accompanying figures, it is envisioned that the light source can be any of a number of types of light sources including but not limited to switchable light sources or passive light sources. Adapter chip 114 can include in-coupling waveguides 128, out-coupling waveguides 126 and combiners 130 which combine the in-coupling and the out-coupling waveguides. Such combiners 130 are well known in the art. Substrate 104 can include waveguides 108 and sensing sites 112 in relation to waveguides 108. For example sensing sites 112 can be on top of and in optical communication with waveguides 108. Detector 106 can include one or more element 116.

In a first embodiment, as shown in FIG. 1A, switchable light source 102 is coupled to and is in optical communication with in-coupling waveguides 128 on adapter chip 114 through optical fibers 118. Optical fibers 118 can be a set of optical fibers as shown in FIG. 1A. Additionally, detector 106 can be coupled to and in optical communication with out-coupling waveguides 126 on adapter chip 114, for example, through a second set of optical fibers 118. Adapter chip 114 can further be coupled and in optical communication with one or more of waveguides 108 at a first edge of substrate 104. Adapter chip 114 of this embodiment and all other embodiments can optionally be configured to provide removable coupling for substrate 104 or other system components described herein. Likewise substrate 104 can further be configured to provide removable coupling with adapter chip 114 or other components of the system.

Figure 1B:
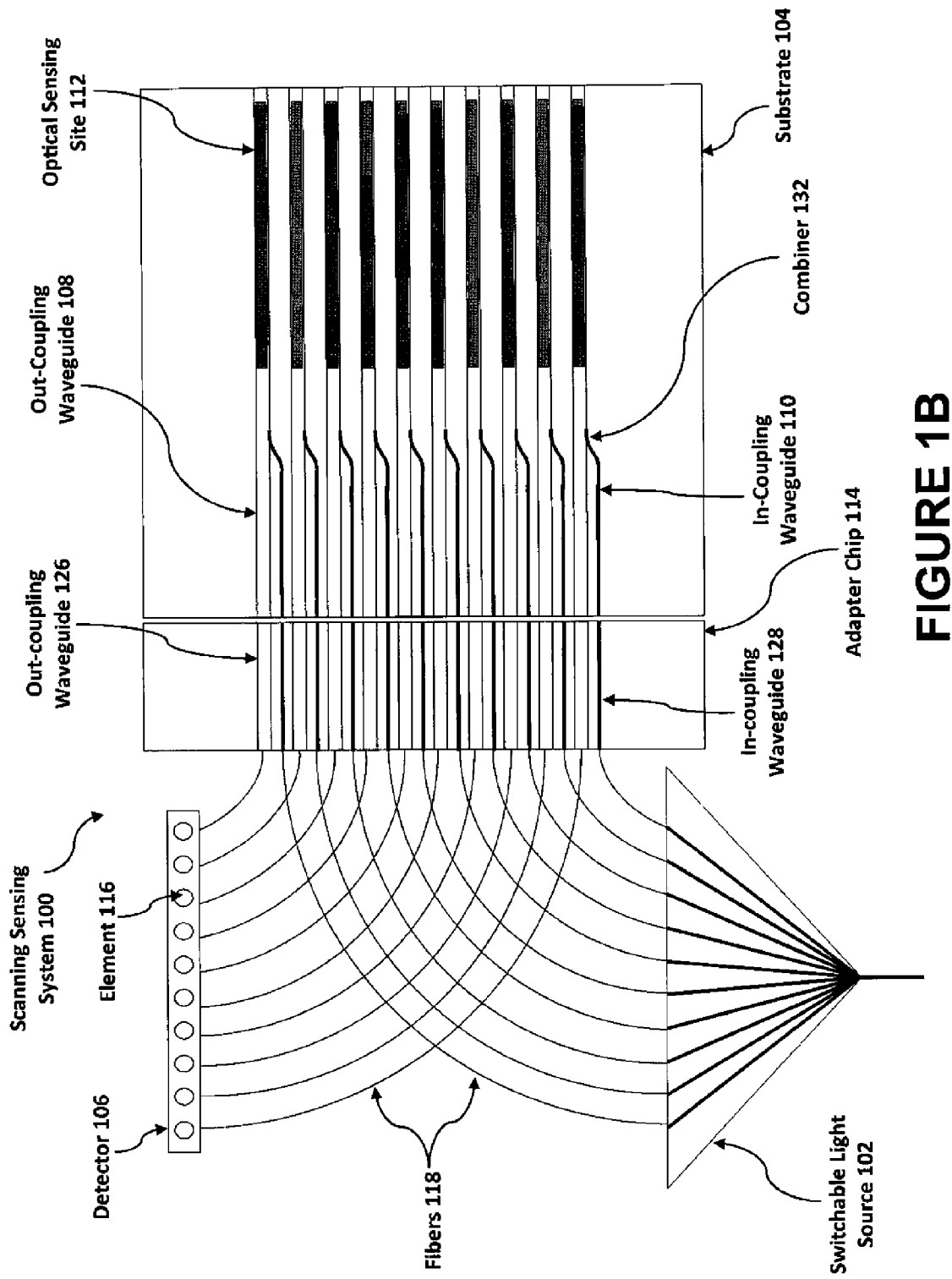
FIG. 1B is a schematic of the scanning sensing system according to another embodiment of the invention including a switchable light source, fibers, an adapter chip, a substrate, optical sensing sites and a detector.

FIG. 1B illustrates an exemplary scanning sensing system 100 of the invention including a switchable light source 102, an adapter chip 114, a substrate 104, optical sensing sites 112 and a detector 106. Adapter chip 114 can include in-coupling waveguides 128 and out-coupling waveguides 126. In this manner Substrate 104 can include in-coupling waveguides 110, out-coupling waveguides 108, combiners 132 which combine in-coupling 110 and out-coupling waveguides 108 and sensing sites 112, for example on top of and in optical communication with out-coupling waveguides 108. Detector 106 can include one or more element 116 as described herein.

In a second embodiment, as shown in FIG. 1B, switchable light source 102 is coupled to and is in optical communication with in-coupling waveguides 128 of adapter chip 114 through a set of optical fibers 118. Additionally, detector 106 is coupled to and in optical communication with out-coupling waveguides 126 of adapter chip 114 through a second set of optical fibers 118. Adapter chip 114 is further coupled to and in optical communication with one or more in-coupling waveguides 110 and with one or more of out-coupling waveguides 108, for example, at an edge of substrate 104.

Figure 1C:
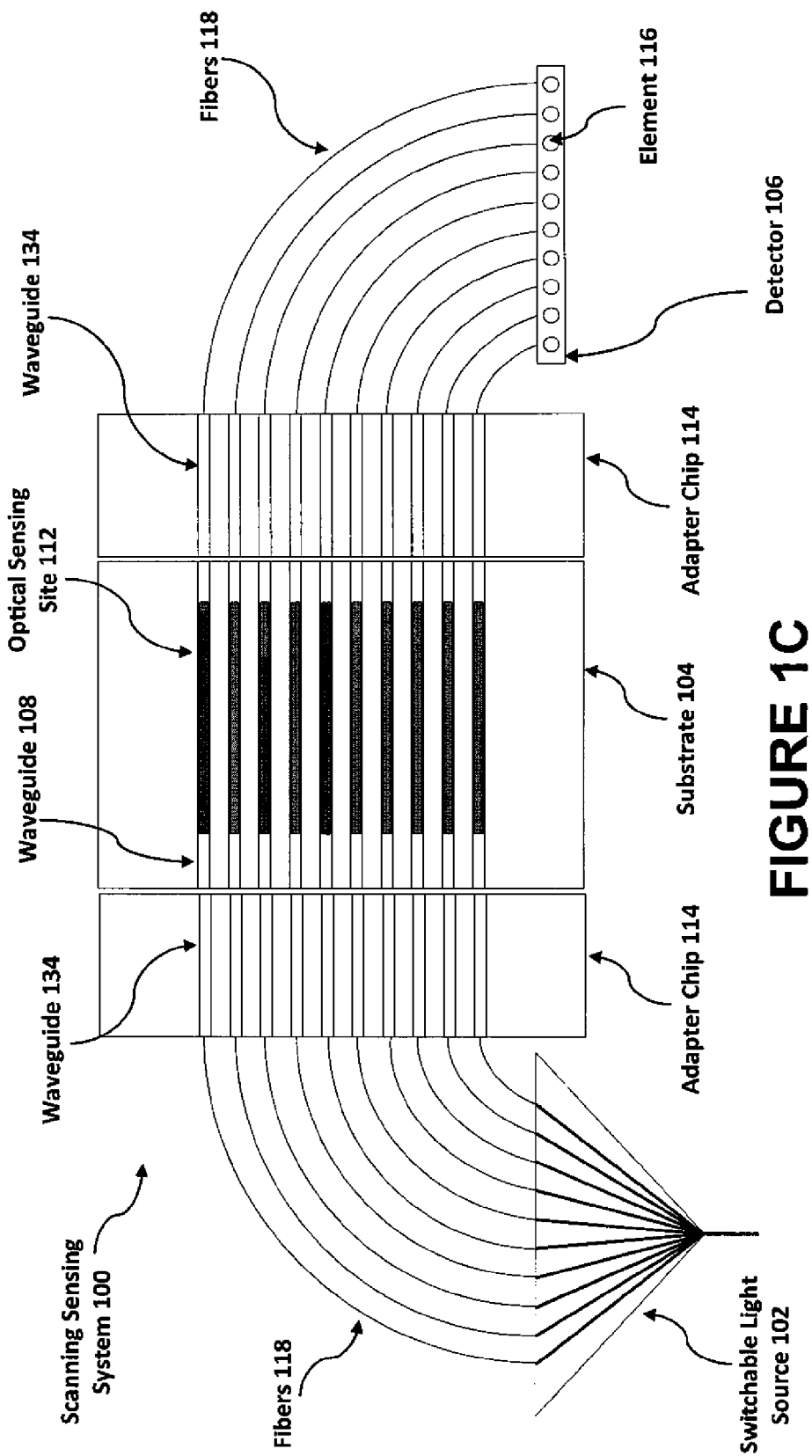
FIG. 1C is a schematic of the scanning sensing system according to another embodiment of the invention a including a switchable light source, fibers, two adapter chips, a substrate, optical sensing sites and a detector.

FIG. 1C illustrates an exemplary scanning sensing system 100 of the invention including a switchable light source 102, two adapter chips 114, a substrate 104, optical sensing sites 112 and a detector 106. The adapter chips include waveguides 134. The substrate includes waveguides 108 and sensing sites 112 on top of and in optical communication with the waveguides.

In a third embodiment, as shown in FIG. 1C, the switchable light source 102 is coupled to and is in optical communication with waveguides 134 on one adapter chip 114 through a set of optical fibers 118. Additionally, detector 106 is coupled to and in optical communication with waveguides 134 on a second adapter chip 114 through a second set of optical fibers 118. The two adapter chips 114 are further coupled and in optical communication with one or more of waveguides 108 at two opposite edges of the substrate 104. As described herein, detector 106 can include one or more elements 116.

Figure 1D:
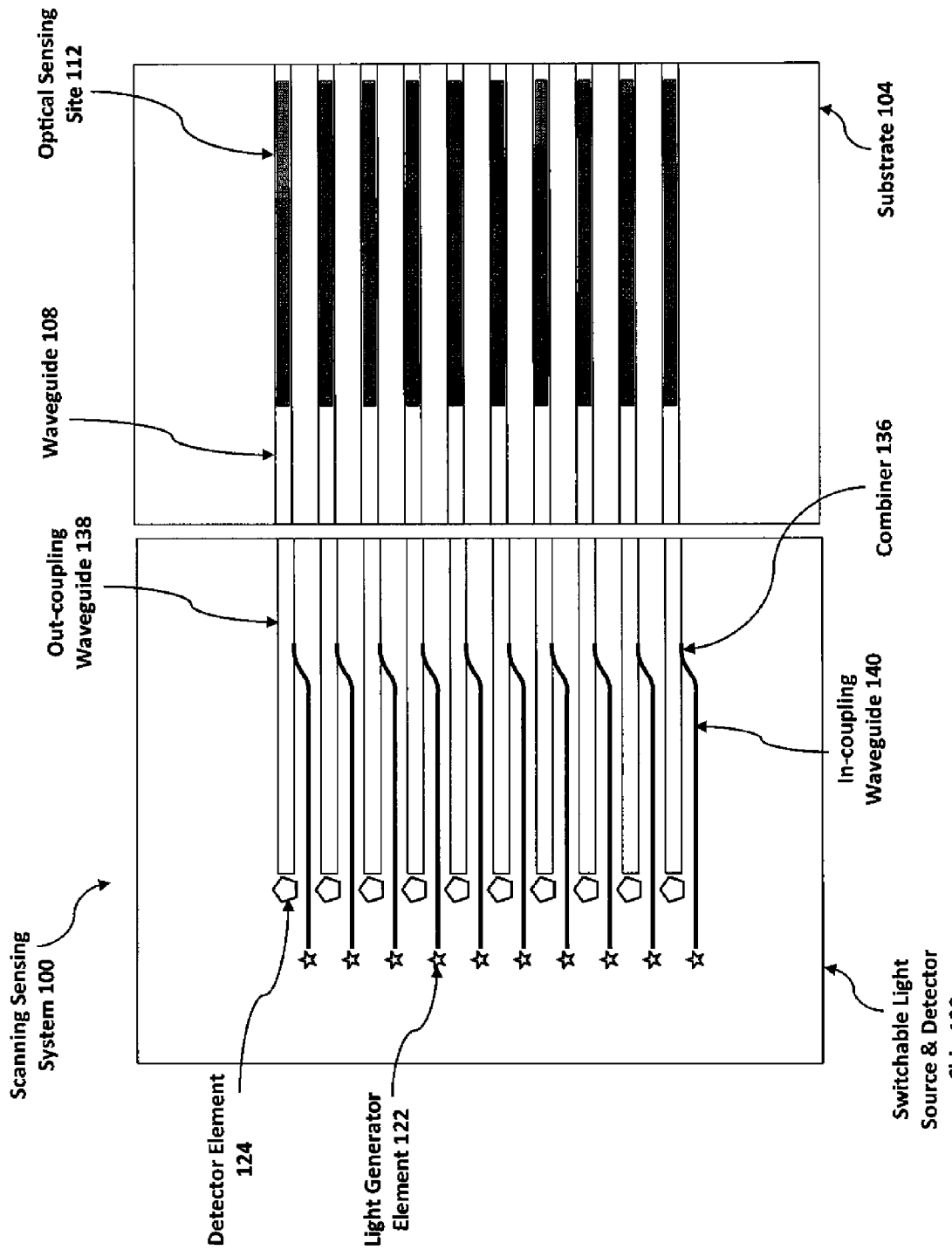
FIG. 1D is a schematic of the scanning sensing system according to another embodiment of the invention including a switchable light source and detector chip, a substrate, and optical sensing sites.

FIG. 1D illustrates an exemplary scanning sensing system 100 of the invention including a combined switchable light source and detector chip 120, a substrate 104 and optical sensing sites 112. The combined switchable light source and detector chip 120 includes light generator elements 122, detector elements 124, combiners 136, out-coupling waveguides 138 and in-coupling waveguides 140. Substrate 104 includes waveguides 108 and optical sensing sites 112 that can be arranged, for example, on top of and in optical communication with waveguides 108.

In a fourth embodiment, as shown in FIG. 1D, light generator elements 122 are coupled to and in optical communication with in-coupling waveguides 140. Additionally, detector elements 124 are coupled to and in optical communication with out-coupling waveguides 138 on the combined switchable light source and detector chip 120. Switchable light source and detector chip 120 is further coupled to and in optical communication with one or more waveguides 108 at an edge of substrate 104.

Although four exemplary embodiments are specifically disclosed herein, it is envisioned that any of a number of other combinations of coupling the different components/chips disclosed herein at different edges of the components/chips are possible. For example, in one embodiment, a first switchable light source and detector chip is coupled to a first edge of the substrate and a second switchable light source and detector chip is coupled at a second edge of the substrate (not shown). It can be understood accordingly that the passage of light waves within the devices and systems described herein, though described in terms of "left" and "right" can be practiced in a variety of directions and orientations based on the flexible arrangements of components provided herein.

As shown in FIGS. 1A to 1D, in some embodiments system 100 can be substantially planar. For example, switchable light source 102 can be a planar chip. This chip can be coupled to a planar adapter chip 114 that is a second chip, that is further coupled to a planar substrate 104 that is a third chip. In a particular embodiment, as shown in FIG. 1A, system 100 is a planar lightwave circuit including three or more coupled planar chips. In one embodiment two chips are integrated into a single chip (e.g., in the switchable light source and detector chip or in an adapter chip and substrate chip). Such a configuration would be useful in a case where the substrate chip is reusable and can be effectively used for long periods of time. One application of such a configuration would be in a system for detecting biological warfare-associated agents. In such an application it would be advantageous for the system to operate for long periods of time without a need for replacing the chip. In addition, having two chips integrated on a single substrate solves the problem of maintaining the relative alignment of two chips (e.g., an adapter chip and substrate chip).

Where the system is used in biological applications, including but not limited to detection of biologically active analytes including nucleic acids, proteins or microorganisms, the substrate can be a multi-element bio-analysis chip.

It is envisioned that an optical sensing site 112 can be associated with each waveguide 108. It is envisioned that the number of optical sensing sites on a substrate chip can be greater than 10, greater than 100, greater than 200, greater than 1,000, great than 5,000 or greater than 10,000. It is further envisioned that the density of optical sensing sites can be greater than 10 per $cm^2$, greater than 100 per $cm^2$, greater than 1,000 per $cm^2$ or greater than 10,000 per $cm^2$. In one embodiment the density of optical sensing sites is greater than 2,000 per $cm^2$.

It is envisioned that in any of the embodiments described herein, that a first light wave generated by the switchable light source in an in-coupling waveguide induces the sensor to transduce an optical signal resulting in a second light wave in an out-coupling waveguide, the second light wave being detectable by the detector.

As illustrated in FIG. 1A, in one advantageous embodiment, System 100 is a planar two-dimensional scanning system. System 100 in this embodiment includes a planar switchable light source 102, for example, a planar optical switch or an array of switchable lasers, coupled to the plane of substrate 104 through a planar adapter chip 114, to make up, for example, a bioanalysis chip plane. Furthermore, switchable light source 102 can provide a dynamic source of light for selective and programmed excitation in respect to individual waveguides 108, providing excitation to part or to all of optical sensing sites 112. A dynamic light source includes but is not limited to a tunable wavelength and/or tunable bandwidth light source. Additionally, system 100 of this embodiment provides for planar collection of the emitted light from all the excited sensing sites 112 in out-coupling waveguides 108, specifically in the plane of substrate 104, such that the light collection is in substantially opposite direction to the light produced in in-coupling waveguides 110.

Figure 2:
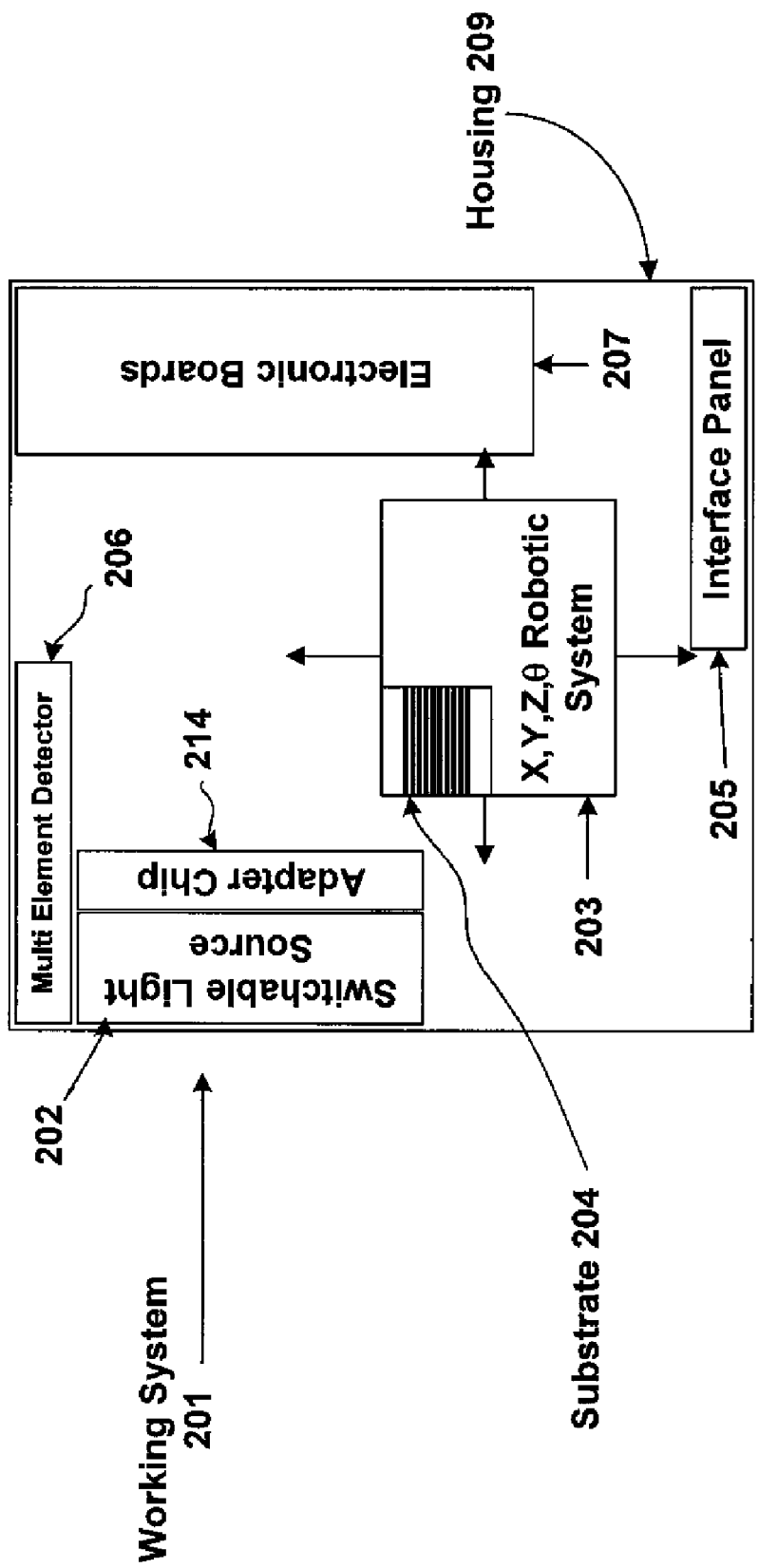
FIG. 2 is block diagram showing the scanning system of the invention in a housing as part of a working system.

FIG. 2 is an exemplary illustration of the scanning system of the invention as part of a working system 201 in a housing 209. While the scanning sensing system illustrated in FIG. 1A-1D is core of the present invention, in order to facilitate the operation of this system, one or more other modules can be included in a working system that includes the scanning sensing system components of the invention.

FIG. 2 illustrates one possible configuration for a working system 201 that can include housing 209 for enclosing various modules of working system 201 including but not limited to substrate 204, robotic system 203, switchable light source 202, adapter chip 214, multi-element detector 206, electronic boards 207 and interface panel 205. Substrate 204, switchable light source 202, and multi-element detector 206, are discussed in detail below.

In regard to housing 209, as shown in FIG. 2, in one embodiment an enclosure or housing 209 holds in place two fixed chips (e.g., of a 3-chip architecture), namely, adapter chip 214, switchable light source 202 and multi-element detector 206. Accordingly, in this embodiment substrate chip 204 is movable in relation to adapter chip 214, switchable light source 202 and multi-element detector 206. Housing 209 can include any number of accurately machined parts and or components as described herein, allowing, for example, the relative alignment of the 3 optical chips. The working system housing can optionally include temperature control and vibration isolation for the working system (not shown).

As shown in FIG. 2, working system 201 can further include an X, Y, Z, θ robotic system 203 for positioning substrate 204 as required within working system 201. X, Y, Z, θ robotic system 203 can be a translation stage with several degrees of freedom for receiving or accepting substrate 204, holding it in place, and aligning it in relation to the rest of working system 201. As desired, at the end of a run X, Y, Z, θ robotic system 203 can eject substrate 204 from working system 201.

It is envisioned that the working system can further include an aligning system (not shown). An aligning system can include one or more light sources, one or more detectors and one or more cameras for active detection of the position of the substrate of the invention. Based on the detected position, the aligning system can align the substrate to the rest of the working system modules, for example, to provide aligned optical communication between the substrate and the switchable light source and detector chip.

As shown in FIG. 2 working system 201 can further include one or more electronic boards 207, for example, an electronic driving board and a control board. It is envisioned that one or more electronic boards can control all the different parts of the working system. Electronic boards 207 can control switchable light source 202 and any other light source present in the system. Electronic boards 207 can be adapted to read any or all of the detectors and cameras in working system 201.

Electronic boards 207 can further be adapted to drive robotic system 203 and control its motion, and optionally monitor and control temperature in different areas of the system. Electronic boards can include logic elements and processors (not shown). It is envisioned that electronic boards can further include embedded software both for controlling the working system and for interfacing the outside world, for example by way of interface panel 205 which can include a key-pad or any other input/output port.

As shown in FIG. 2 working system 201 can additionally include one or more interface panel 205. It is anticipated that the system will have one or more interface panel 205 to allow a user to interface with the system and operate it. Interface panels can include any number of input and output ports well known in the art for connecting the system to other systems or to an external control console (not shown).

Figure 3A:
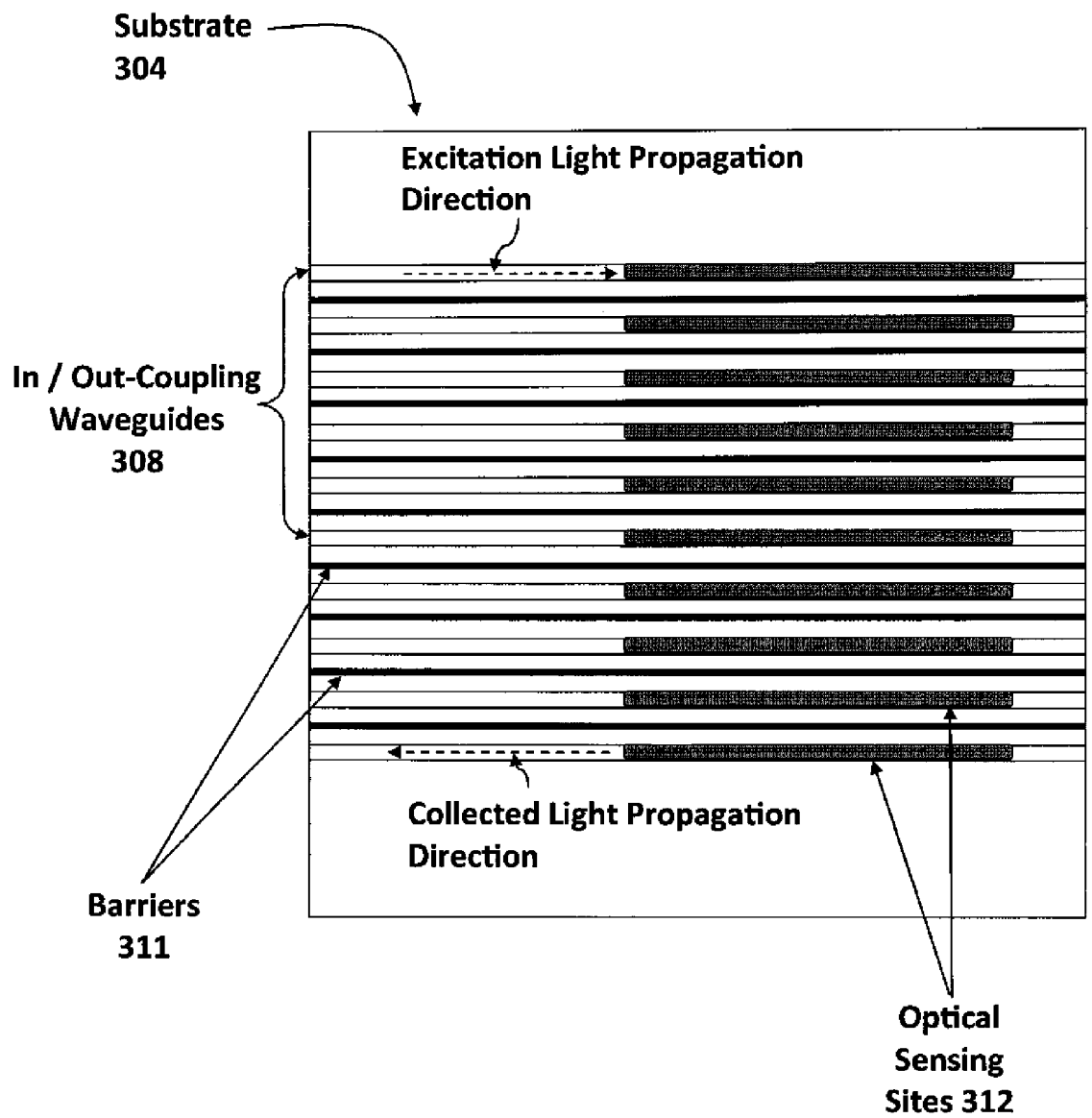
FIG. 3A is a schematic of the substrate of the invention according to one embodiment including optical waveguides in conjunction with optical sensing sites and barriers.

FIG. 3A illustrates an exemplary substrate 304 of the system of the first embodiment of the current invention further including barriers 311 intended to block stray light within the substrate and reduce crosstalk between the different elements of the substrate. Barriers 311 can be light absorbing or light reflecting. Barriers 311 can be variously sized, shaped and positioned between waveguides 308 in any of a number of orientations to achieve a desired optical effect. As shown in FIG. 3A, barriers 311 can be arranged between two adjacent waveguides and proximal to optical sensing sites 312. Waveguides 308 are used to guide a primary light wave (excitation light; see dashed arrow) from the left edge of substrate 304 to optical sensing sites 312. Waveguides 308 then guide a secondary light wave (collected at optical sensing sites 312; see dashed arrow) from optical sensing sites 312 back to the left edge of substrate 304.

Figure 3B:
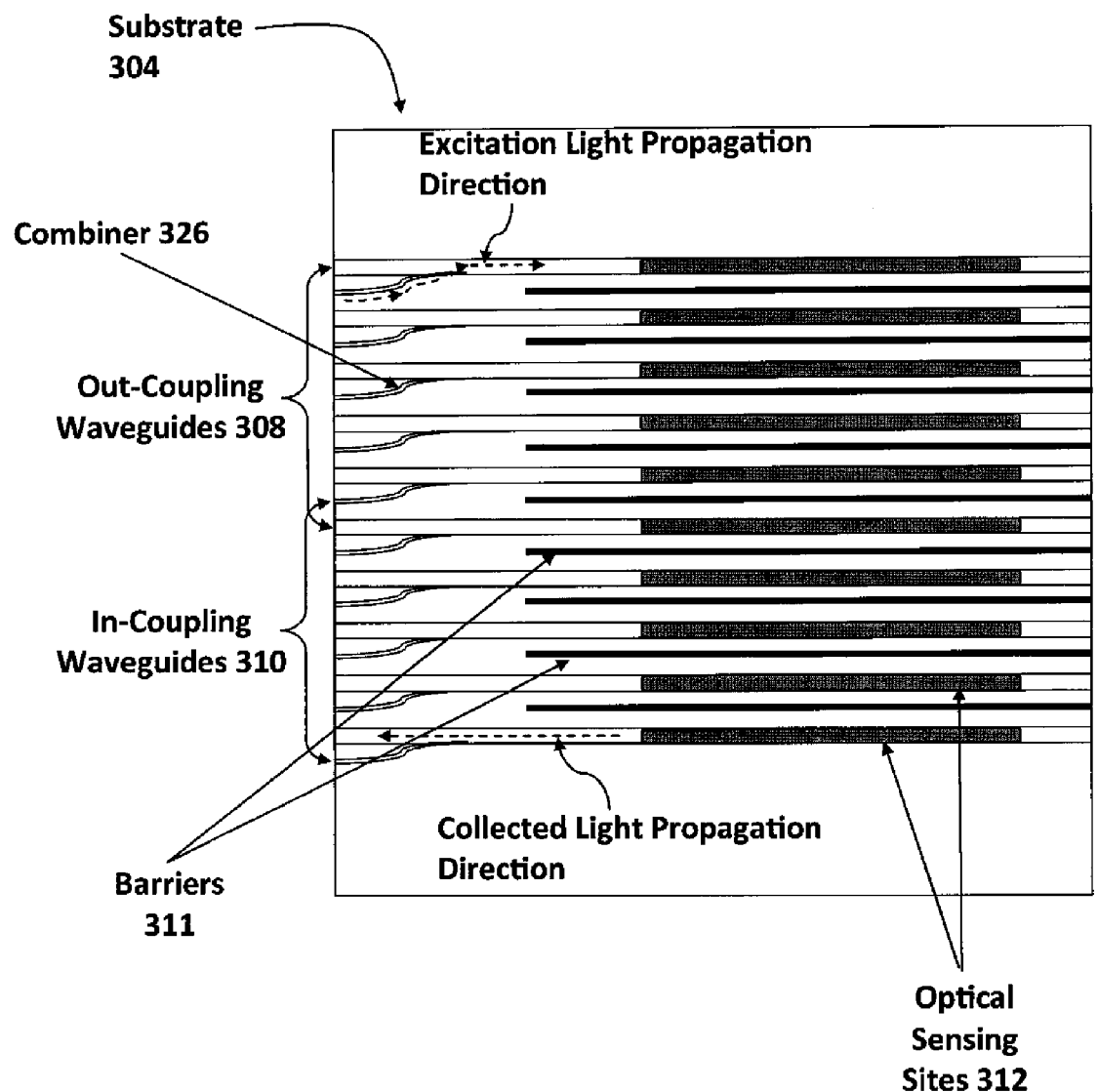
FIG. 3B is a schematic of the substrate of the invention according to another embodiment including optical waveguides and combiners in conjunction with optical sensing sites and barriers.

FIG. 3B illustrates an exemplary substrate 304 of the system of the second embodiment of the current invention further including in-coupling waveguides 310 and combiners 326. The primary light wave (excitation light; see dashed arrow) is coupled to substrate 304 through in-coupling waveguides 310 at the left edge of substrate 304. The excitation light traveling from left to right is combined by combiners 326 into out-coupling waveguides 308 which further guides it to optical sensing sites 312. Out-coupling waveguides 308 are then used to guide the secondary light wave (collected at sensing sites 312; see dashed arrow) from optical sensing sites 312 back to the left edge of substrate 304. Barriers 311 have the same purpose as described above in FIG. 3A.

Figure 3C:
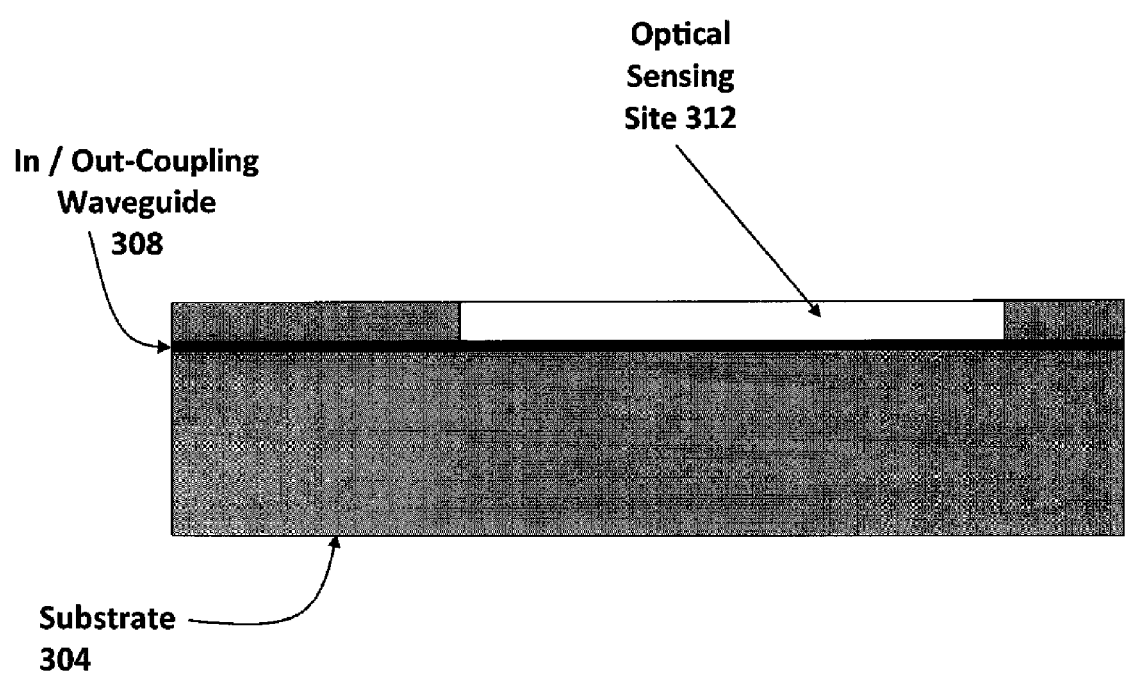
FIG. 3C is a schematic cross section of the substrate of the invention according to one embodiment including an optical waveguide in conjunction with an optical sensing site.

FIG. 3C schematically illustrates a cross section of the substrate 304 of the current invention. In the example illustrated, in/out coupling waveguides 308 are embedded underneath a surface of substrate 304. Optical sensing sites 312 can be etched into a surface, for example, the upper cladding of substrate 304 and located, for example, adjacent and on top of waveguide 308 facilitating optical communication between them. It is envisioned that in a different embodiment, the optical sensing sites can also be located on the surface of substrate 304 or etched only part of the way into the upper cladding, or all the way through the waveguides (not shown). It is also envisioned that the waveguides can be single-mode waveguides, multi-mode waveguides or any combination of the two, namely, single mode in the vertical dimension and multi-mode in the lateral dimension.

Figure 4A:
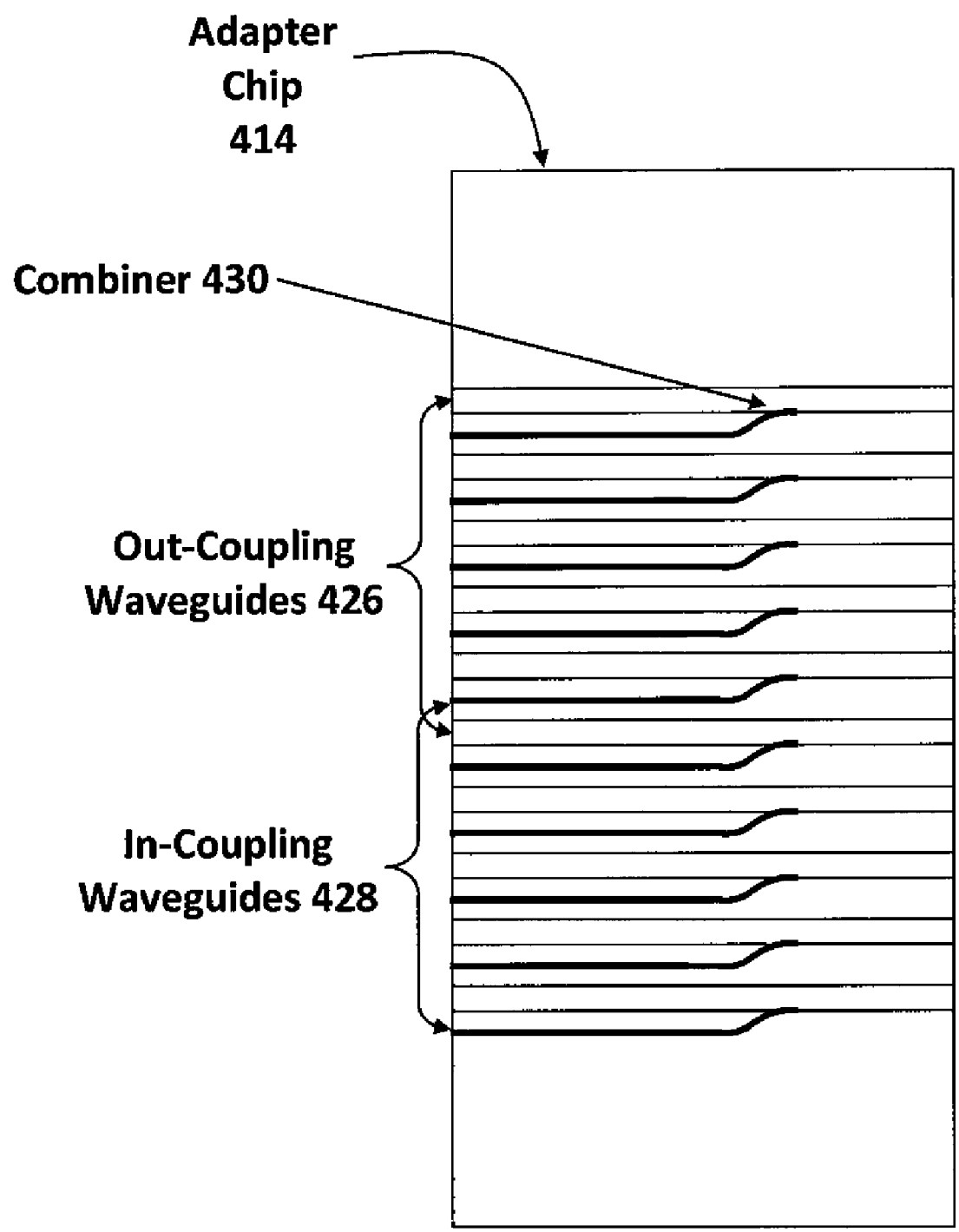
FIG. 4A is a schematic of the adapter chip of the invention according to one embodiment including optical in-coupling and out-coupling waveguides and the optical combiners.

FIG. 4A illustrates the adapter chip 414 of the first embodiment (see FIG. 1A) of the current invention. The adapter chip 414 includes in-coupling waveguides 428, out-coupling waveguides 426 and combiner 430. A primary light wave (excitation light) can be coupled from left into in-coupling waveguides 428. The excitation light is then combined by combiners 430 into waveguides 426 which then guides it to the right edge of adapter chip 414 and couples it out to the substrate (not shown). The substrate (not shown) couples back the secondary light wave (collected at the optical sensing sites—not shown) to out-coupling waveguides 426 at the right edge of adapter chip 414. The secondary light wave is guided by waveguides 426 from right to left and is coupled out of adapter chip 414 at its left edge to the detector (not shown).

Figure 4B:
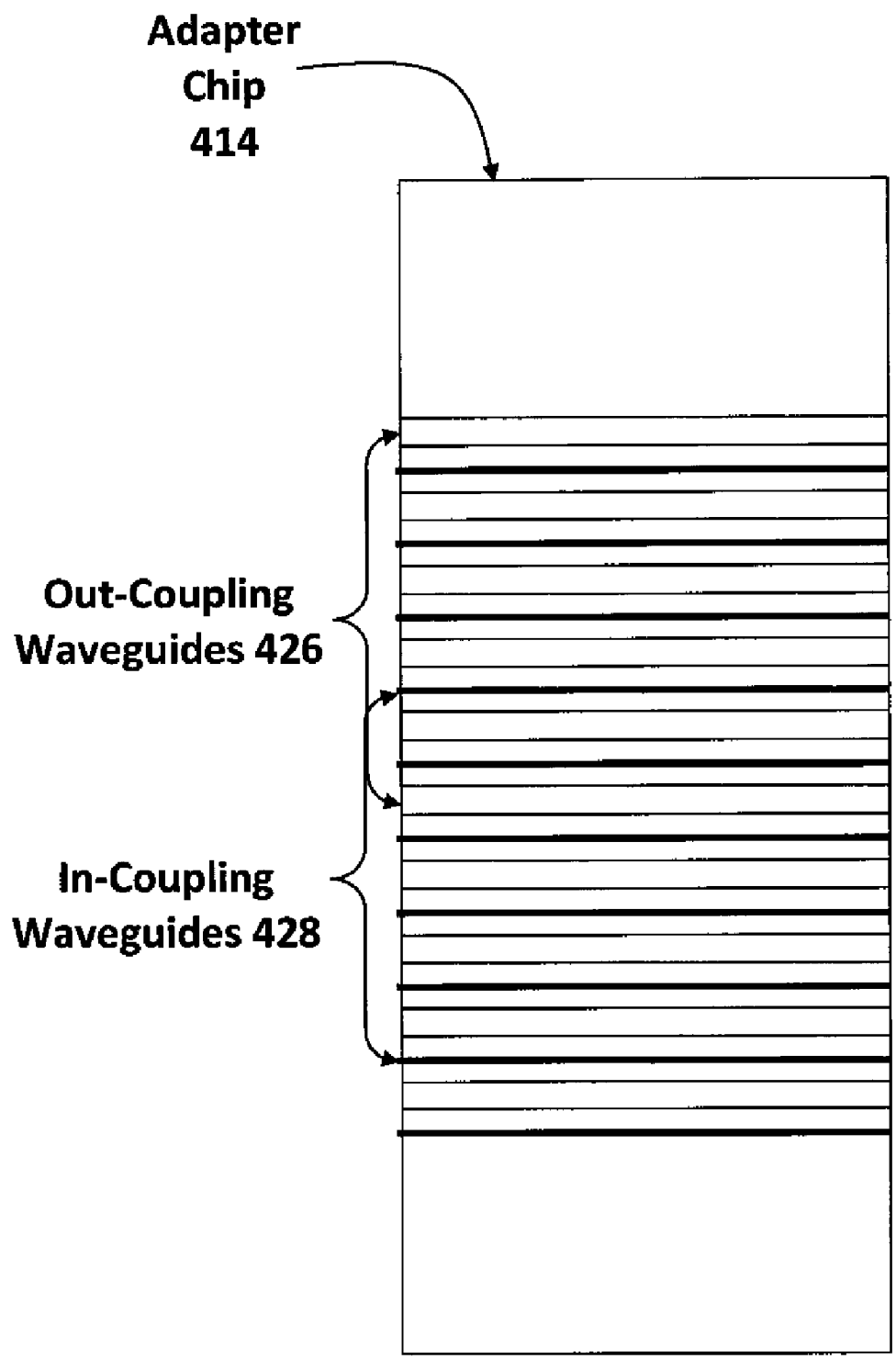
FIG. 4B is a schematic of the adapter chip of the invention according to the second embodiment including the optical in-coupling and out-coupling waveguides.

FIG. 4B illustrates adapter chip 414 of the second embodiment (see FIG. 1B) of the current invention. Adapter chip 414 includes in-coupling waveguides 428 and out-coupling waveguides 426. A primary light wave (excitation light) can be coupled from left into in-coupling waveguides 428. Waveguide 428 guides the primary light wave to the right edge of the adapter chip 414 and couples it out to the substrate (not shown). The substrate (not shown) couples back the secondary light wave (collected at the optical sensing sites—not shown) to out-coupling waveguides 426 at the right edge of adapter chip 414. The secondary light wave is guided by waveguides 426 from right to left and is coupled out of adapter chip 414 at its left edge to the detector (not shown).

A range of dimensions for the various features described herein include: waveguides thickness—20 nm to 50 μm; waveguide width—1 μm to 500 μm; waveguide length—1 mm to 100 mm; optical sensing site length—100 μm to 100 mm; optical sensing site width—1 μm to 500 μm; optical sensing site depth—0 to 20 μm; waveguide pitch—10 μm to 10 mm; substrate thickness—100 μm to 5 mm; upper cladding thickness—0 to 20 μm; and lower cladding thickness—0.1 μm to 20 μm.

Figure 4C:
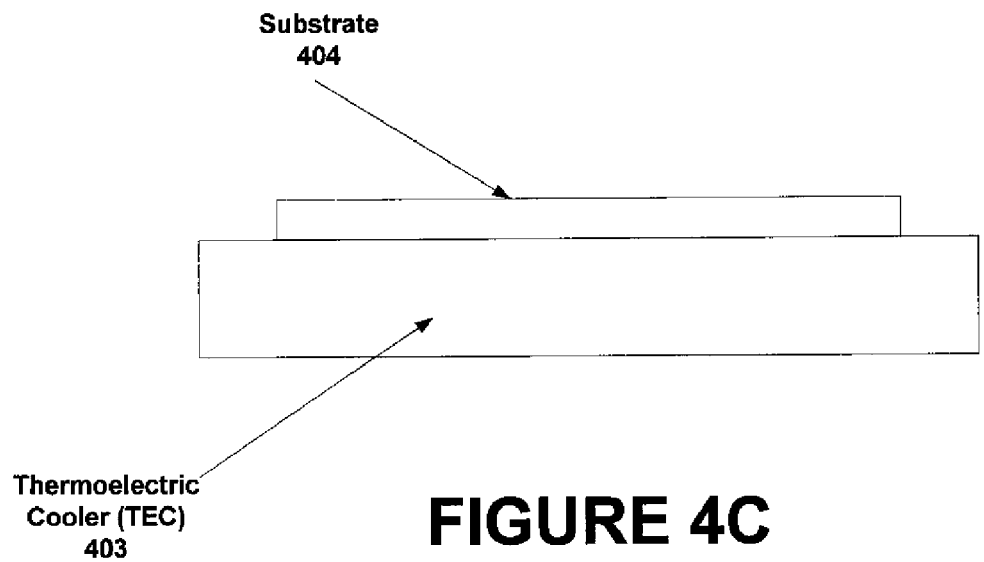
FIG. 4C is a schematic of a side view of the substrate in relation to a thermoelectric cooler.

FIG. 4C in a side view illustrates another embodiment of substrate 404 of the invention in relation to a thermal transfer element 403, for example, a thermoelectric cooler (TEC). Thermal transfer element 403 is a temperature control system useful for heating or cooling a chip, for example, substrate 404. Although the thermal transfer element may be referred to herein as a cooling element, it is to be understood that where the thermal transfer element is configured to increase and decrease the temperature of a chip, the component functions essentially as a heating and as a cooling element depending on the induced direction of the electrical current. The thermal transfer element can provide a range of useful temperatures. For example, the thermal transfer element can be configured to provide a temperature in the range between about −40° C. to about 120° C. as desired. As illustrated in FIG. 4C, thermal transfer element 403 can be adapted to receive substrate 404 of the invention. Thermal transfer element 403 can be adapted to contact part or all of a surface of substrate 404 of the invention.

Providing thermal transfer element 403 in conjunction with substrate 404 of the invention is useful, for example, for the amplification of tested sample molecules through processes such as Polymerase Chain Reaction (PCR) as described herein. In use, the embodiment as described for FIG. 4C provides the capability of controlling the temperature of the entire substrate such that as the temperature of the entire substrate is cycled, samples at any optical sensing site can be amplified by PCR simultaneously.

Figure 4D:
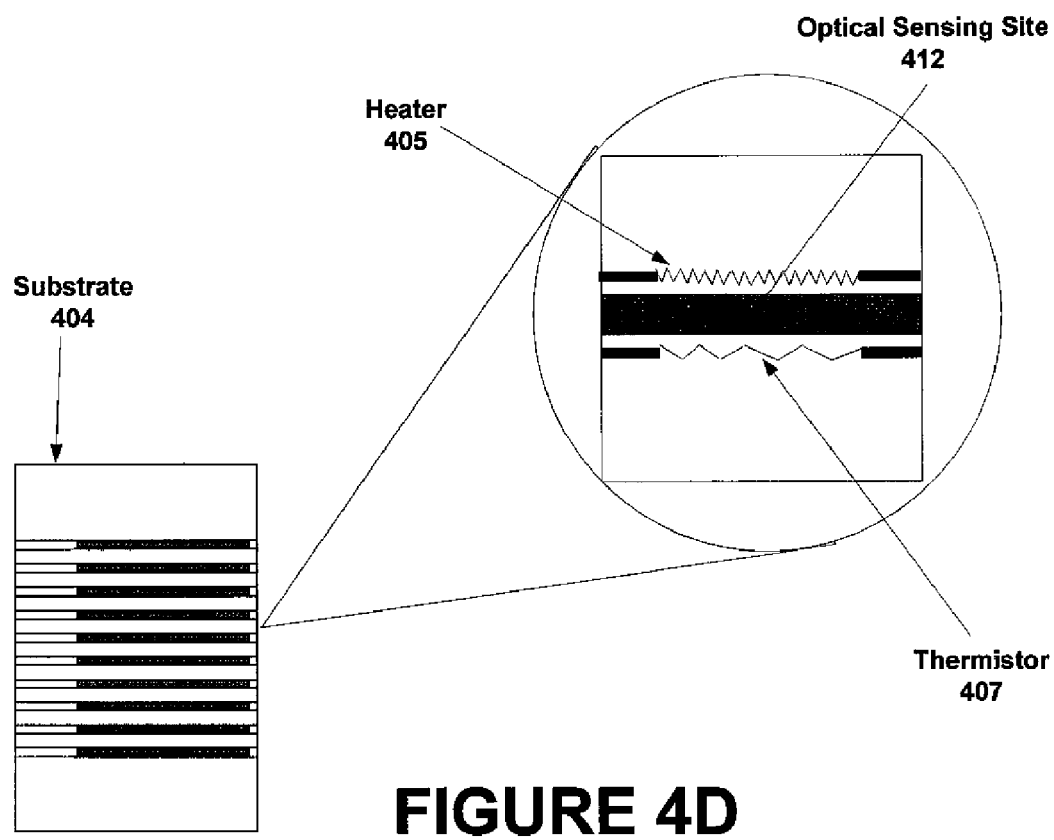
FIG. 4D is a schematic of the substrate of the invention illustrating details of an optical sensing site including a heater and a thermistor.

FIG. 4D illustrates another embodiment of substrate 404 of the invention wherein optical sensing site 412 includes heater 405 and thermistor 407. In this embodiment, optical sensing site 412 of substrate 404 can include heater 405, for example, a thin-film heater, in the vicinity of one or more sensing site 412. Heater 405 can be adapted to enable individual temperature control for each sensing site 412. In addition to heater 405, thermistor 407 can be located at or near one or more sensing site 412 thereby providing for measuring the local temperature. In use, this embodiment provides the capability of running the same or any desired different number of cycles and the same or any desired different temperature profiles for each and every sensing site.

The adapter of the various embodiments described herein can include a plurality of optical elements comprising at least one lens and at least one filter, wherein the plurality of optical elements are configured to manipulate and couple light from the light source to the substrate and further configured to manipulate and couple light from the substrate to the detector. It is envisioned that the optical elements can be individual elements including lenses and/or filters. It is further envisioned that the optical elements can have a size configuration that is suitable for interfacing with the light source, substrate, detector and other elements of the systems described herein.

Advantageously, the embodiments described for FIGS. 4C and 4D can support real-time PCR. As described herein, since optical detection is done from within the substrate, signal detection in both embodiments (see FIGS. 4C and 4D) can be done while the samples are in the process of the amplification cycles, thereby enabling real time analysis of the PCR process.

Figure 4E:
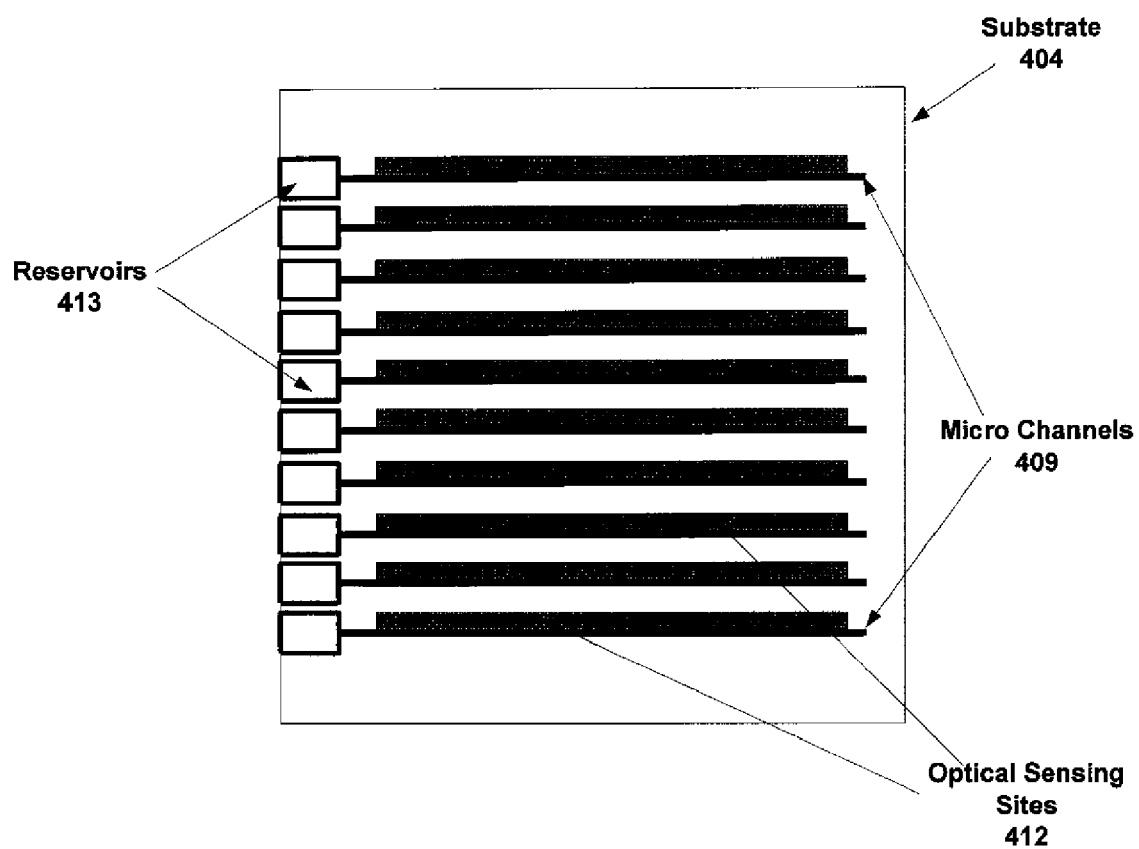
FIG. 4E is a schematic of the substrate of the invention including reservoirs and micro channels in relation to optical sensing sites.

FIG. 4E illustrates yet another embodiment of substrate 404 of the invention wherein substrate 404 additionally includes reservoirs 413 and microchannels 409 in relation to optical sensing sites 412. As such, in this embodiment microfluidics are incorporated into the substrate. Microfluidics can be adapted to drive liquid (in this case the tested sample) using the capillary effect across the substrate. As illustrated in FIG. 4E, this can be achieved by an arrangement of microchannels 409, optionally of varying width, which force the sample from one or more reservoirs 413 to optical sensing sites 412 which can include etched wells to receive the sample. The microchannels can be either etched on the face of the chip itself or can be added as an external structure on a surface of the substrate 404.

In use, it is envisioned that a sample to be tested can be pipetted into a reservoir at one end of the substrate. The sample can then be distributed using the microfluidic system to the optical sensing sites and sensing wells where it is allowed to bind to pre-spotted probes and can subsequently be optically scanned and analyzed. Several reservoirs may be used to separate different samples/patients or for running several parallel tests.

The substrate of the scanning sensing system can made up of any of a number of well known materials suitable for use in planar lightwave circuits. For example, useful substrate materials include but are not limited to Silica ($SiO_2$), glass, epoxy, lithium niobate and indium phosphide as well as combinations thereof. The waveguides disclosed herein can be made up of Silicon, Silica ($SiO_2$) and derivatives thereof, silicon oxynitride (SiON) and derivatives thereof, silicon nitride (SiN) and derivatives thereof, polymers, lithium niobate and indium phosphide as well as combinations thereof. In one embodiment, UV light is used to change the refractive index of a waveguide material after deposition.

Figure 5A:
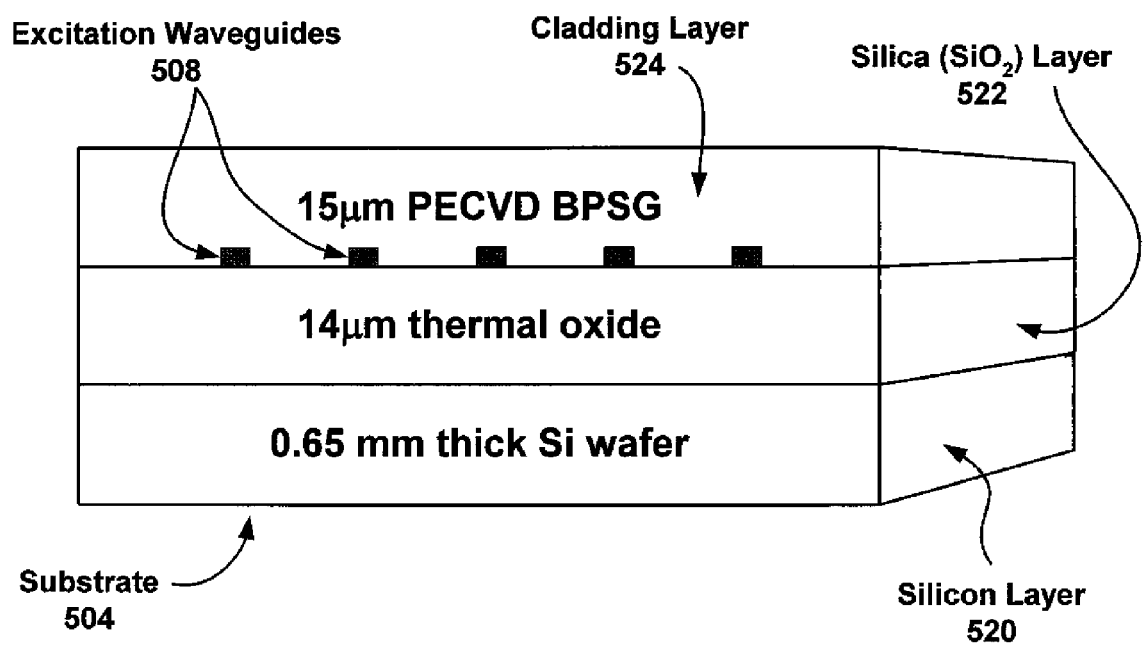
FIG. 5A is a schematic of a general substrate including typical layers and waveguides representative of those of the current invention.

FIG. 5A illustrates an exemplary silicon layer 520 of the substrate 504. For example, the silicon layer 520 can be made up of a silicon wafer having a thickness from about 0.1 mm to 10 mm. In another example the silicon wafer can have a thickness from about 0.3 to 1 mm. In a particular example as illustrated in FIG. 5A, the silicon wafer has a thickness of 0.65 mm. As shown in FIG. 5A in one embodiment, the silica ($SiO_2$) layer 522 is a 14 μm thermal oxide layer of Silica ($SiO_2$) created by placing the Silicon in an oxygen-rich environment inside a furnace at high temperature. The top Silicon layer oxidizes over time (several hours) creating a $SiO_2$ layer.

Additionally, as shown in FIG. 5A, in one embodiment, the cladding layer 524 is 15 μm thick and deposited by a PECVD (Plasma-Enhanced Chemical Vapor Deposition) process after etching to produce the waveguides 508.

It is envisioned that the various layers of the substrate can include different refraction index properties. For example, a waveguide layer (e.g. SiN) has a higher refraction index than a cladding layer of silica deposited thereon.

Figure 5B:
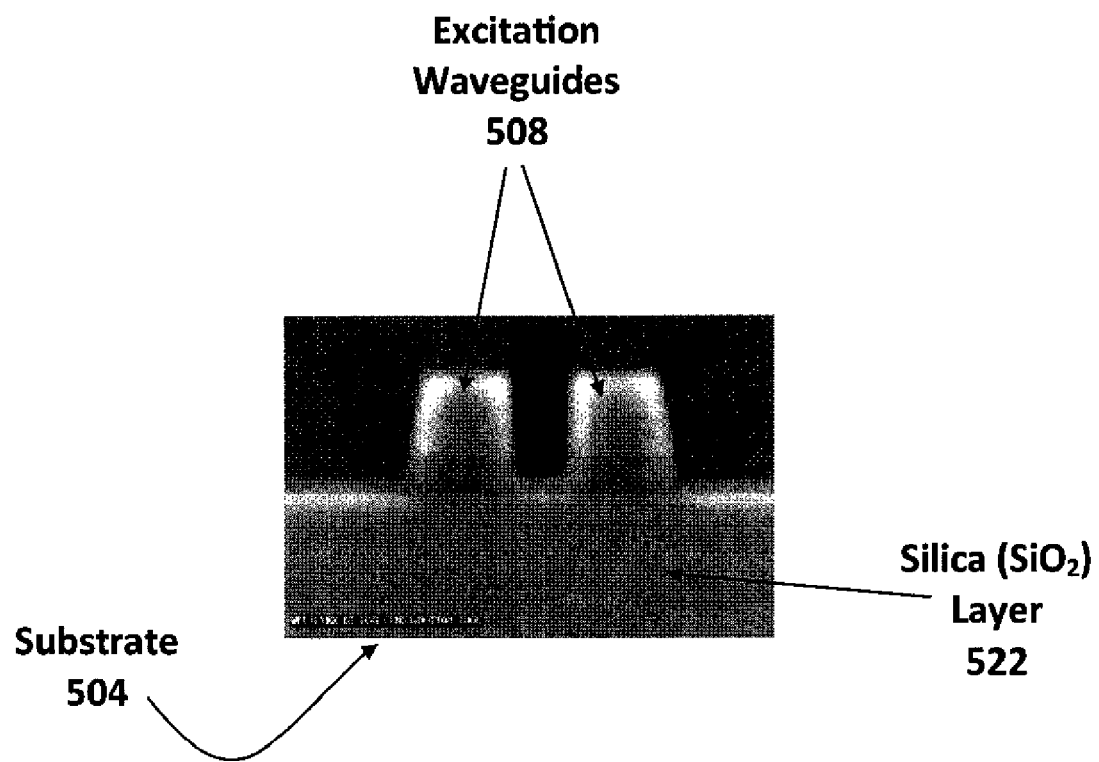
FIG. 5B is a photomicrograph image of waveguides representative of those of the invention and a silica layer.
Figure 5C:
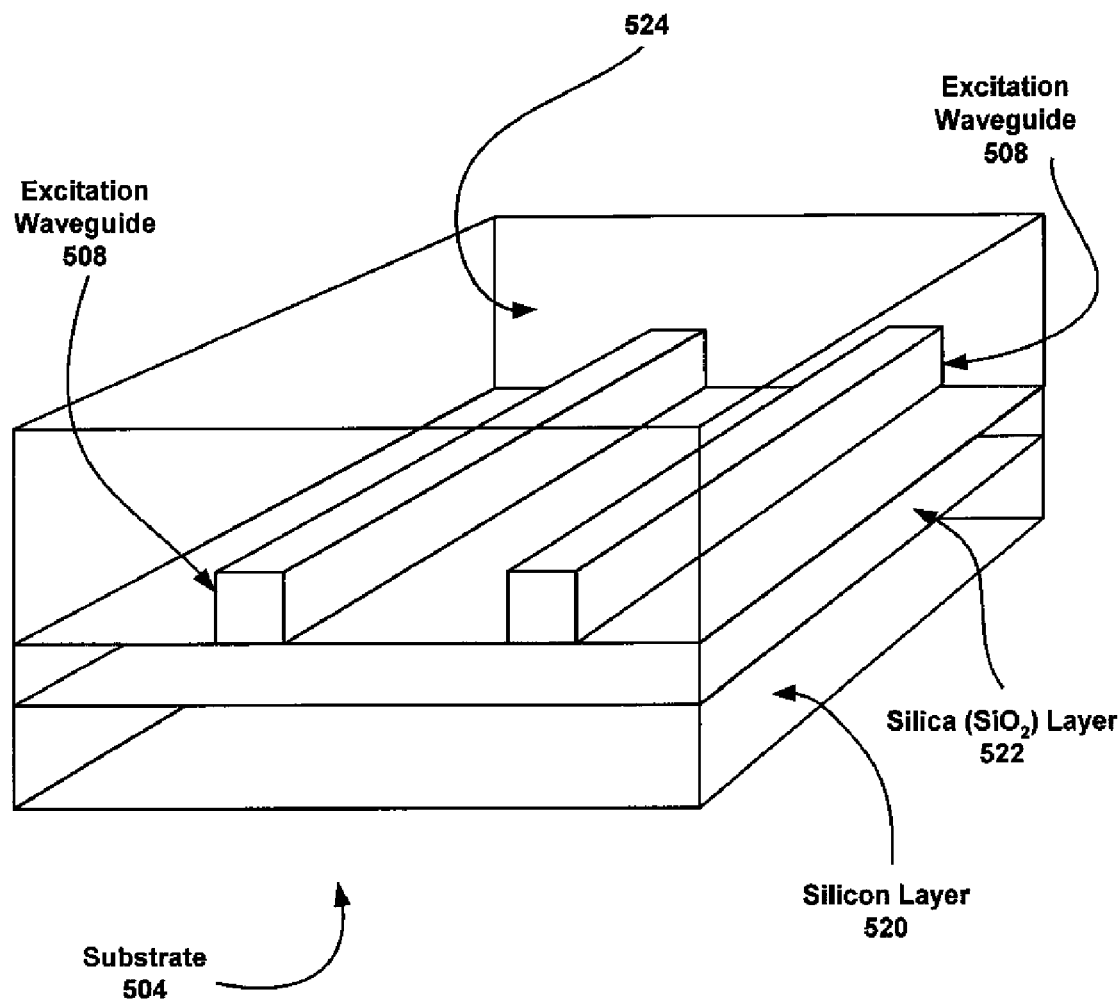
FIG. 5C is a perspective view of waveguides and associated substrate layers.

As shown in FIG. 5B (illustrated with a photomicrograph prior to deposition of a cladding layer), in some embodiments, the substrate 504 can include two waveguides 508 arranged for light wave coupling on a silica (SiO2) layer 522. Alternatively, as shown in FIG. 5C, two waveguides 508 can be arranged for guiding uncoupled light waves on a silica (SiO2) layer 522 and over-clad with a cladding layer 524.

The optical sensing sites in one embodiment are in the form of wells, for example, etched wells (see FIG. 3C cross-section view). Where the optical sensing site is a well, it can act as a vessel for a liquid sample. In another embodiment the optical sensing sites are a region on the surface of the substrate, for example, above the waveguides. In a further embodiment, the optical sensing sites are biochemical interaction sites. For example, where the optical sensing site is a well containing a sensor single stranded DNA oligonucleotide having a fluorescent tag attached, a solution containing a target complementary single stranded DNA added to the well could biochemically interact by base-pairing with the sensor within the optical sensing site (not shown). In another example the optical sensing site is a location or well containing one or more immunoassay reagent for conducting an immunoassay as described herein.

In a particular embodiment, the optical sensing sites comprise optical transducers (not shown). An optical transducer is defined as any device that generates a measurable change (wavelength, amplitude or phase) to the incoming primary light wave and can thus be monitored in the outgoing secondary light wave. In one embodiment the optical transducers are fluorescence wells including fluorescent or luminescent compounds, wherein light waves guided by the waveguides excite the fluorescent or luminescent compound in the wells in the presence of a target, and the same waveguides collect and guide light emitted from the wells to the detector (through the adapter chip), for example at the edge of the chip (not shown).

The sensor of the optical sensing site of the system can be a sensor that discriminates or interacts with a target (e.g., a biologically active analyte) in a sample from, for example, a biological, man-made or environmental source. As discussed above, a first lightwave can induce the sensor to transduce an optical signal to a second light wave. In one embodiment where the sensor is capable of discriminating or interacting with a target in a sample, a measurable change in the second light wave can result when the sensor discriminates or interacts with the target. Upon detection of the change in the second light wave using the detector of the system, presence of the target in the sample is known.

Any of a number of sensors can be used with the scanning sensing system to measure phenomenon associated with sensing of a target in a sample. Examples of suitable sensors include, but are not limited to, a fluorescence well or cell, an absorption cell, an interferometric sensor, a diffractive sensor or a Surface Plasmon Resonance (SPR) detector. For a fluorescence well or cell, the phenomenon measurable can be light emission from luminescent or fluorescent molecular tags. For example, emitted light at an altered wavelength can be measured. In the case of an absorption cell, changes in the sample optical density (OD) can measurably affect the intensity of the light passing through the sample. For an interferometric sensor, changes in the effective refractive index of a waveguide generate a phase different between two light waves leading to different interference patterns measurable as a difference in intensity at the detector. For a diffractive sensor, changes in the effective refractive index at the surface of a diffractive element, for example, a grating, affect the diffraction angle of the light for a given wavelength or alternatively affect the wavelength at a given diffraction angle. In the case of a SPR sensor, changes in the effective refractive index at a metal-dielectric interface affect the resonance conditions for generating surface Plasmons.

Figure 6A:
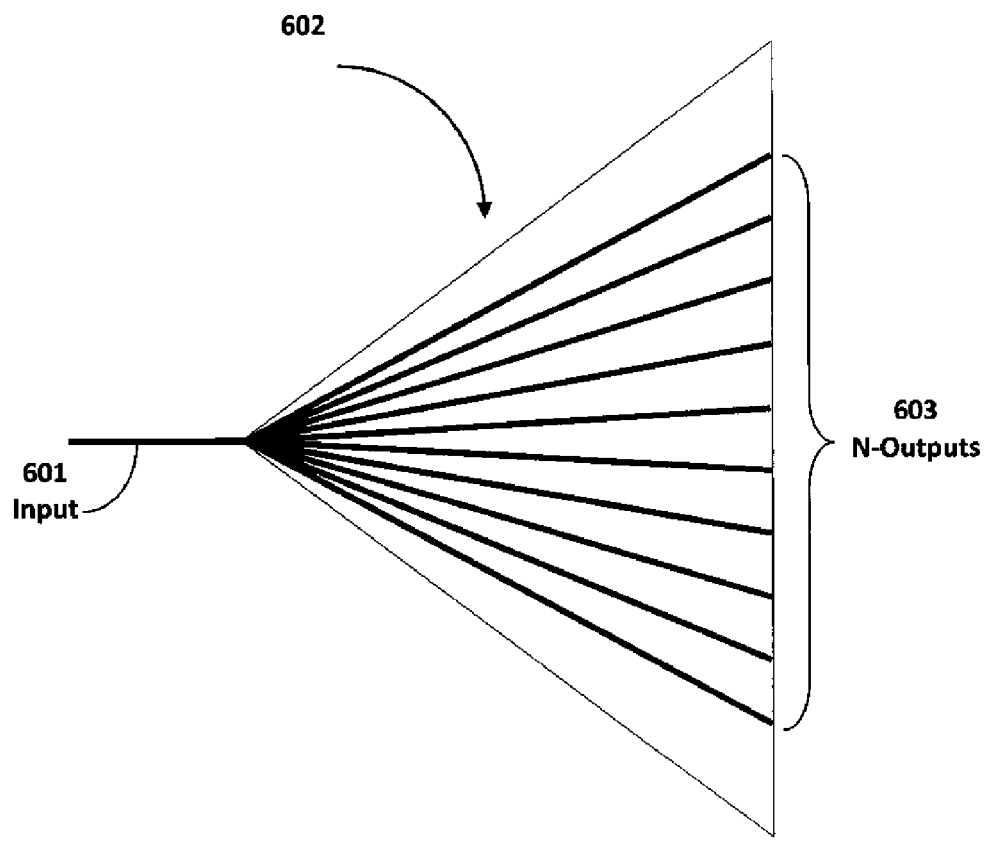
FIG. 6A is a schematic of a switchable light source of the invention including inputs and outputs.

FIG. 6A illustrates an exemplary switchable light source 602 of the system of the invention, including one or more inputs 601 as a primary source of light for coupling to a light generator. The light generator can be any source of electromagnetic radiation emitting one or more discrete spectrallines or a continuous spectrum (not shown). In one preferred embodiment the light generator is a laser source emitting in one or more well defined wavelengths. In a second preferred embodiment the light generator is a tunable laser that can be tuned to emit light in one wavelength within a predefined range. As illustrated, switchable light source 602 further includes a plurality of outputs 603 shown in FIG. 6A as N-Outputs. The number of outputs 603 included in switchable light source 602 can be variable based on the intended use. For example, in certain applications the number of outputs 603 can be greater than 10 outputs. In one embodiment the number of outputs 603 can be great than 100 outputs. In a further embodiment the number of outputs 603 can be greater than 1,000 outputs. In another embodiment the number of outputs 603 ranges from about 50 to 500.

The light source can be a passive 1×N splitter with N being for example, between 1 and 1,000. It is further envisioned that N can be greater than 1,000, greater than 10,000 or greater than 100,000. Such an arrangement is advantageous in that is allows for simultaneous (e.g. parallel) excitation in waveguides of the system as described herein.

Figure 6B:
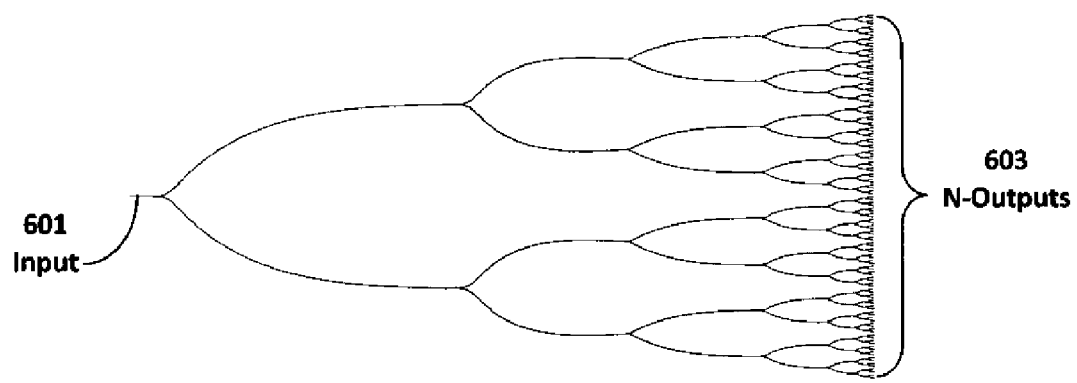
FIG. 6B is a schematic of a branched architecture between the inputs and outputs of a switchable light source of the invention.

In a particular embodiment, the number of outputs 603 is about 128. As shown in FIG. 6A, in one embodiment, the switchable light source includes outputs 603 that fan out from an input 601 equally splitting the light at input 601 to all outputs 603. As illustrated in FIG. 6B, in one embodiment a branched architecture stemming from the input 601 to the outputs 603 can be used. Although only one input is shown in FIGS. 6A and 6B, it is envisioned that multiple inputs 601 can be used.

Figure 6C:
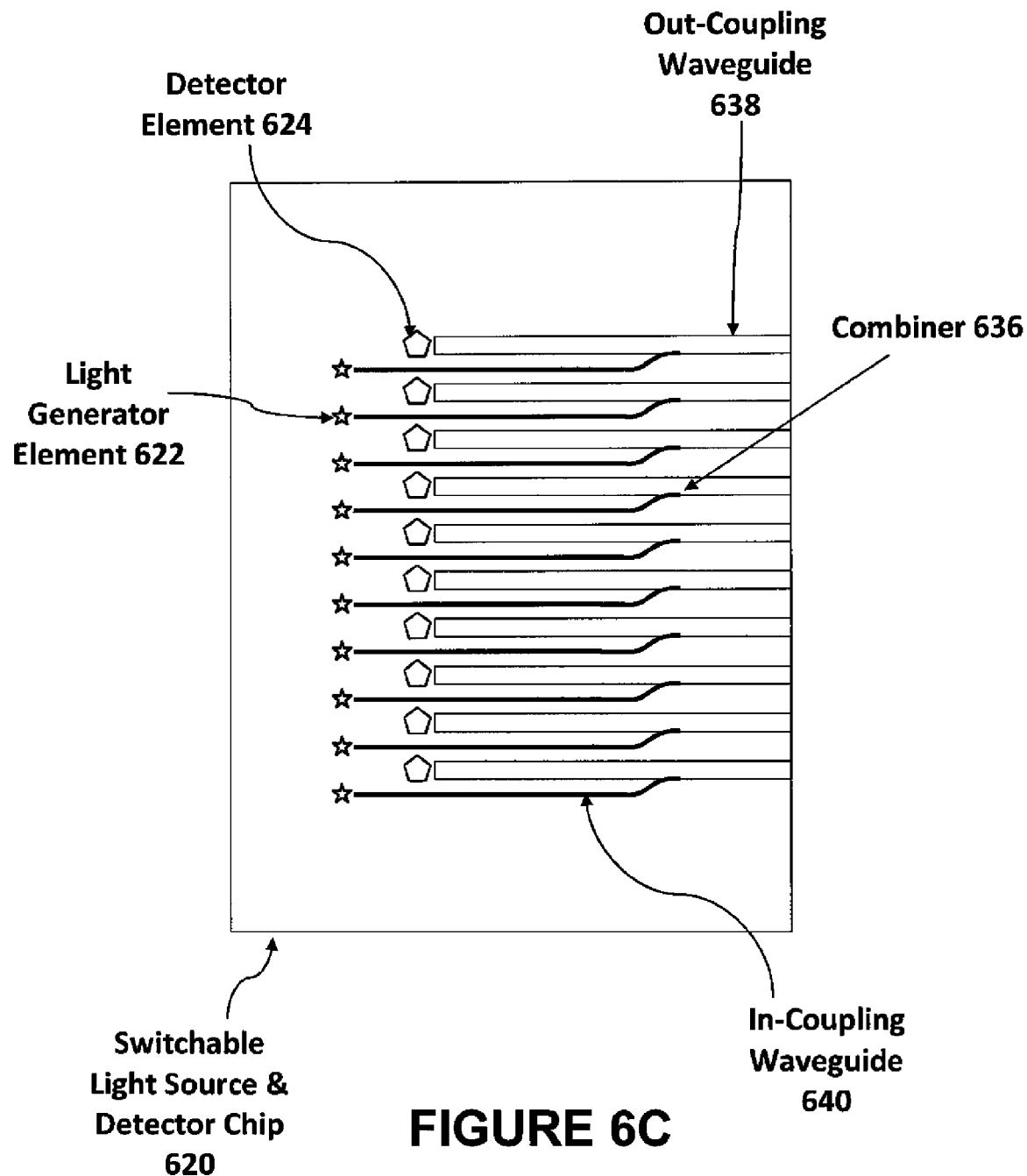
FIG. 6C is a schematic of one embodiment of a switchable light source and detector chip of the invention including light generator elements, detector elements, in-coupling and out-coupling waveguides and combiners.

FIG. 6C illustrates an exemplary switchable light source and detector chip 620 of one system of the invention including light generator elements 622, detector elements 624, in-coupling waveguides 640, out-coupling waveguides 638 and combiners 636. Light generator elements 622 generate a primary light wave which is coupled to in-coupling waveguides 640. The light wave propagates from left to right and is combined by combiners 636 out-coupling waveguides 638. At the right edge of switchable light source and detector chip 620 the primary light wave couples out to the substrate (not shown). A secondary light wave generated at the optical sensing sites on the substrate (not shown) is coupled back to switchable light source and detector chip 620 at its right edge and propagates from right to left guided by out-coupling waveguides 638 and into detector elements 624. In this embodiment light generator elements 622 and detector elements 624 are connected through, for example, electronic leads (not shown) to an external electronic control and driver board (not shown) which controls and drives light generator elements 622 and detector elements 624.

It is envisioned that the switchable light source can be a dynamic light source allowing for selective and programmed generation of the primary light wave through one or more individual output. In one embodiment the switchable light source is an optical switch, for example, a planar optical switch. The switchable light source can be a light manipulating device for switching light from a given input to any given output. Moreover, the switchable light source can multicast an input light to several outputs all at the same time. In one embodiment, switchable light source is an optical switch coupled to a light generator through one or more optical fiber (not shown). In a particular embodiment, the light generator is coupled to one or more of the inputs of the switchable light source. By way of non-limiting examples, the light generator can provide variable wavelengths of light. In one embodiment, the light generator is a broad-band source. In another embodiment, the light generator is a tunable source.

The switchable light source can include K (=1, 2, 3 ...) inputs and N output. In some embodiments, the number of outputs will be equal to the number of in-coupling waveguides in the substrate of the system. In a particular embodiment, the interface between a light generating source and the switchable light source inputs includes optical fibers. The interface between the switchable light source and detector chip outputs should match, in terms of pitch, the in-coupling waveguides in the substrate to allow these two elements to butt-couple and transfer light from the switchable light source and detector chip to the in-coupling waveguides on the substrate.

In one embodiment the optical switch includes individual switching elements based on Mach Zehnder interferometers.

The light source and detector chip can include an array of light generator elements. In one implementation, the light generator elements are light emitting diodes (LED). In another implementation the light generator elements are laser chips. Each individual light generator element is separately controlled and can be turned on or off as desired. In one implementation the light source and detector chip includes 10 or more light generator elements. In another implementation the light source and detector chip includes 100 or more light generator elements. In yet another implementation the light source and detector chip includes 1000 or more light generator elements. In a particular implementation the light source and detector chip includes between 10 and 100 light generator elements.

The light source and detector chip can include an array of detector elements. In one implementation, the detector elements are PIN diodes. In another implementation the detector elements are Avalanche Photo-Diodes (APD). Each individual detector element is separately controlled and read. In one implementation the light source and detector chip includes 10 or more detector elements. In another implementation the light source and detector chip includes 100 or more detector elements. In yet another implementation the light source and detector chip includes 1000 or more detector elements. In a particular implementation the light source and detector chip includes between 10 and 100 detector elements.

The light generator elements array on the light source and detector chip can be integrated on a single chip with the detector elements array. Such a chip includes an array of two or more light generator elements, an array of two or more detector elements, an array of two or more in-coupling waveguides, an array of two or more out-coupling waveguides and an array of two or more combiners. In one implementation each light generator element is optically coupled to one in-coupling waveguide and adapted such that most of the light emitted by the light generator element propagates along that waveguide. The waveguides can extend to the edge of the chip where they can be brought to couple the light propagating within them to the substrate. In one implementation two light generator elements, each optionally emitting at a different wavelength can be coupled to a single in-coupling waveguide. In another implementation more than two light generator elements, each optionally emitting at a different wavelength can be coupled to a single in-coupling waveguide.

The light source and detector chip can include in addition to a light generator elements, detector elements and waveguides, light manipulating features such as filters, switches, modulators, splitters, combiners, mirrors and circulators.

The control of the light source and detector chip can be either integrated on the same chip as the light generator elements, detector elements and waveguides or alternatively can be external to the chip. The light source and detector chip can have an electrical interface to an external driver or external controller or logic interface to an external control system. The control of the light source and detector chip allows driving each light generator element and each detector element separately. It further allows also control of the other features present on the light source and detector chip such as, for example, the modulators and switches.

The light source and detector chip can couple to the substrate in several different ways. In one implementation the coupling is done by bringing the ends of the waveguides on both chips (the light source and detector chip and the sensing substrate) in close proximity and allowing the light to flow directly from one waveguide to the other. In another implementation, a portion of the waveguides on both chips are aligned on top of each other, parallel and in close proximity to each other, thus coupling light from one waveguide to the other through the evanescent electromagnetic field.

All coupling schemes described between the light source and detector chip and the sensing substrate apply to the coupling between the adapter chip and the sensing substrate.

Additional elements useful in planar lightwave circuits, including but are not limited to couplers, filters, mirrors, circulators, splitters, modulators, switches and trenches are envisioned as part of the system described herein (not shown). Such elements when integrated into the sensing substrate or into the light source and detector chip can serve to manipulate the incoming first light waves in the in-coupling waveguides or outgoing second light waves in the out-coupling waveguides.

Figure 7:
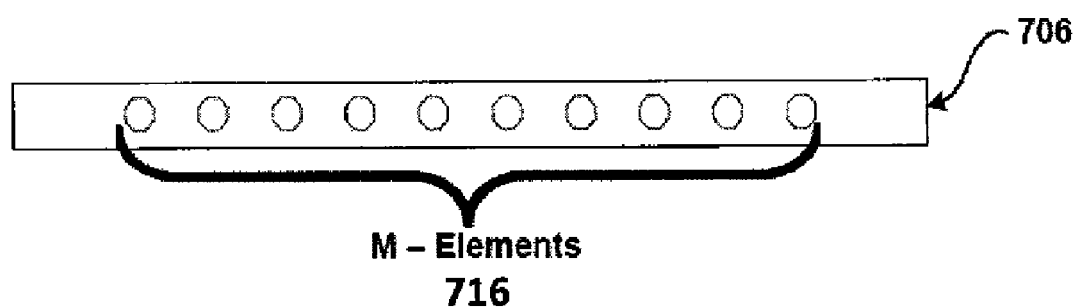
FIG. 7 is a schematic of a detector of the invention.

FIG. 7 illustrates an exemplary detector 706 of the system of the invention including elements 716 (shown as M-elements). In one embodiment, as shown in FIG. 7, the detector 706 includes an array of light sensitive elements 716, for example, in the form of a photodetector array, In one embodiment, as shown in FIG. 1A, the number of elements 116 matches the number of out-coupling waveguides 126 in the adapter chip 114.

In one non-limiting example, the detector is a detector array having a spectral range of between 400 to 1000 nm, a photosensitivity (A/W) of >0.3, an active area per element of 0.005 mm$^2$, 128 elements, and a pitch of <0.1 mm.

In one embodiment, the detector is a silicon photodiode (PN, PIN or APD) array. An example of a suitable detector array is the Texas Advanced Optoelectronic Solutions (TAOS) 1×128 linear array (PN-TSL1210R).

A control system for managing the different steps of operating the scanning sensing system is envisioned.

The control system can manage steps such as alignment of the light source and detector chip, sensing substrate and adapter chip, in addition to switching the light output from the light source, reading the detector array and reporting the results detected.

In practicing the methods of the present invention, many conventional techniques in molecular biology are optionally utilized. These techniques are well known and are explained in, for example, Ausubel et al. (Eds.) *Current Protocols in Molecular Biology, Volumes I, II, and III,* (1997), Ausubel et al. (Eds.), *Short Protocols in Molecular Biology: A Compendium of Methods from Current Protocols in Molecular Biology,* 5th Ed., John Wiley & Sons, Inc. (2002), Sambrook et al., *Molecular Cloning: A Laboratory Manual,* 3rd Ed., Cold Spring Harbor Laboratory Press (2000), and Innis et al. (Eds.) *PCR Protocols: A Guide to Methods and Applications, Elsevier Science & Technology Books* (1990), all of which are incorporated herein by reference.

Sample preparation suitable for use with the system and methods described herein can include any of a number of well know methods for collection and analysis of biological and/or environmental samples. In the case of biological samples the sample can be, for example, manipulated, treated, or extracted to any desired level of purity for a target of interest.

The sample can be bodily fluids suspected to contain a biologically active analyte. Commonly employed bodily fluids include but are not limited to blood, serum saliva, urine, gastric and digestive fluid, tears, stool, semen, vaginal fluid, interstitial fluids derived from tumorous tissue, and cerebrospinal fluid.

It is anticipated that the systems described herein can be used for screening a large variety of samples. In the case where the investigated subject is a living creature, the sample may originate from body fluids as discussed. Methods of obtaining samples include but are not limited to cheek swabbing, nose swabbing, rectal swabbing, skin fat extraction or other collection strategies for obtaining a biological or chemical substance. When the tested subject is a non-living or environmental body, the sample may originate from any substance in a solid phase, liquid phase or gaseous phase. The sample may be collected and placed onto the sensing substrate or the sensing substrate may be directly exposed to the investigated sample source (e.g. water reservoir, free air) and interact with it.

In some embodiments, the bodily fluids are used directly for detecting one or more biologically active analyte present therein with the subject scanning sensing device without further processing. Where desired however, the bodily fluids can be pre-treated before performing the analysis with the subject scanning sensing devices. The choice of pre-treatments will depend on the type of bodily fluid used and/or the nature of the biologically active analyte under investigation. For instance, where the biologically active analyte is present at low level in a sample of bodily fluid, the sample can be concentrated via any conventional means to enrich the biologically active analyte. Methods of concentrating a biologically active analyte include but are not limited to drying, evaporation, centrifugation, sedimentation, precipitation, and amplification. Where the biologically active analyte is a nucleic acid, it can be extracted using various lytic enzymes or chemical solutions according to the procedures set forth in Sambrook et al.

("Molecular Cloning: A Laboratory Manual"), or using nucleic acid binding resins following the accompanying instructions provided by manufactures. Where the biologically active analyte is a molecule present on or within a cell, extraction can be performed using lysing agents including but not limited to denaturing detergent such as SDS or nondenaturing detergent such as thesit (2-dodecoxyethanol), sodium deoxylate, Triton® X-100, and Tween® 20.

In some embodiments, pretreatment can include diluting and/or mixing the sample, and filtering the sample to remove, e.g., red blood cells from a blood sample.

Targets detectable using the scanning sensing system include but are not limited to, a biologically active analyte including a nucleic acid, a protein, an antigen, an antibody, a microorganism, a gas, a chemical agent and a pollutant.

In one embodiment, the target is a nucleic acid that is DNA, for example, cDNA. In a related embodiment, the DNA target is produced via an amplification reaction, for example, by polymerase chain reaction (PCR). In another embodiment of the subject invention, the detected biologically active analyte is a protein representing a known biomarker for a disease or specific condition of the investigated organism. In another embodiment several different biologically active analytes can be proteins provided as a panel of bio-markers wherein relative concentrations of the bio-markers are indicative for a disease or other condition of the investigated organism. In a further embodiment the target is a microorganism that is a pathogen. In another embodiment the target is a chemical agent, for example, a toxic chemical agent.

Where the target is a nucleic acid, it can be single-stranded, double-stranded, or higher order, and can be linear or circular. Exemplary single-stranded target nucleic acids include mRNA, rRNA, tRNA, hnRNA, ssRNA or ssDNA viral genomes, although these nucleic acids may contain internally complementary sequences and significant secondary structure. Exemplary double-stranded target nucleic acids include genomic DNA, mitochondrial DNA, chloroplast DNA, dsRNA or dsDNA viral genomes, plasmids, phage, and viroids. The target nucleic acid can be prepared synthetically or purified from a biological source. The target nucleic acid may be purified to remove or diminish one or more undesired components of the sample or to concentrate the target nucleic acids. Conversely, where the target nucleic acid is too concentrated for the particular assay, the target nucleic acid may be diluted.

Following sample collection and optional nucleic acid extraction, the nucleic acid portion of the sample comprising the target nucleic acid can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target nucleic acid. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target nucleic acid is single-stranded, the first cycle of amplification forms a primer extension product complementary to the target nucleic acid. If the target nucleic acid is single stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3, from the 3' nucleotide of the primer used to replicate that complementary template strand in the PCR.

The target nucleic acid can be amplified by contacting one or more strands of the target nucleic acid with a primer and a polymerase having suitable activity to extend the primer and copy the target nucleic acid to produce a full length complementary nucleic acid or a smaller portion thereof. Any enzyme having a polymerase activity that can copy the target nucleic acid can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB D DNA polymerases; RNA polymerases such as *E. coli*, SP6, T3 and T7 RNA polymerases; and reverse transcriptases such as AMV, M MuLV, MMLV, RNAse H' MMLV (Superscript®), Superscript® II, ThermoScript®, HIV 1, and RAV2 reverse transcriptases. All of these enzymes are commercially available. Exemplary polymerases with multiple specificities include RAV2 and Tli (exo) polymerases. Exemplary thermostable polymerases include Tub, Taq, Tth, Pfx, Pfu, Tsp, Tfl, Tli and *Pyrococcus* sp. GB D DNA polymerases.

Suitable reaction conditions are chosen to permit amplification of the target nucleic acid, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot start techniques, use of nested primers, or designing PCR primers so that they form stem-loop structures in the event of primer-dimer formation and thus are not amplified. Techniques to accelerate PCR can be used, for example, centrifugal PCR, which allows for greater convection within the sample, and comprising infrared heating steps for rapid beating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target nucleic acids or different regions of a particular target nucleic acid within the sample.

Amplified target nucleic acids may be subjected to post amplification treatments. For example, in some cases, it may be desirable to fragment the target nucleic acid prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow a nucleic acid associated with the optical sensing site to hybridize to the amplification product during at least part of an amplification cycle. When the assay is performed in this manner, real time detection of this hybridization event can take place by monitoring for light emission during amplification.

Real time PCR product analysis (and related real time reverse-transcription PCR) provides a well-known technique for real time PCR monitoring that has been used in a variety of contexts, which can be adapted for use with the methods described herein (see, Laurendeau et al. (1999) "*TaqMan PCR-based gene dosage assay for predictive testing in individuals from a cancer family with INK4 locus haploinsufficiency*" Clin Chem 45(7):982-6; Bièche et al. (1999) "*Quantitation of MYC gene expression in sporadic breast tumors with a real-time reverse transcription-PCR assay*" Cancer Res 59(12):2759-65; and Kreuzer et al. (1999) "*LightCycler technology for the quantitation of bcr/abl fusion transcripts*" Cancer Res 59(13):3171-4, all of which are incorporated by reference). In addition, linear PCR and Linear-After-The Exponential (LATE)-PCR can be adapted for use with the methods described herein.

Immunoassays can be conducted on the scanning sensor system of the invention, for example, at one or more optical sensing site of the system. Suitable immunoassay systems include but are not limited to competitive and noncompetitive assay systems. Such assay systems are typically used with techniques such as western blots, radioimmunoassays, EIA (enzyme immunoassay), ELISA (enzyme-linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein. A immunoassays, and cellular immunostaining (fixed or native) assays to name but a few. Such assays are routine and well known in the art (see, e.g., Ausubel et al., supra). Immunoassay techniques particularly useful with the scanning sensor systems described herein include but are not limited to ELISA, "sandwich" immunoassays, and fluorescent immunoassays. Exemplary immunoassays are described briefly below (but are not intended by way of limitation).

ELISAs generally involve preparing antigen, coating a well (e.g., an optical sensing site of the scanning sensor system) with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

In one exemplary immunoassay, a sample contains an unknown amount of biologically active analyte to be measured, which may be, for example, a protein. The analyte may also be termed an antigen. The sample may be spiked with a known or fixed amount of labeled analyte. The spiked sample is then incubated with an antibody that binds to the analyte, so that the analyte in the sample and the labeled analyte added to the sample compete for binding to the available antibody binding sites. More or less of the labeled analyte will be able to bind to the antibody binding sites, depending on the relative concentration of the unlabeled analyte present in the sample.

Accordingly, when the amount of labeled analyte bound to the antibody is measured, it is inversely proportional to the amount of unlabeled analyte in the sample. The amount of analyte in the original sample may then be calculated based on the amount of labeled analyte measured, using standard techniques in the art.

In one exemplary competitive immunoassay, an antibody that binds to a biologically active analyte may be coupled with or conjugated with a ligand, wherein the ligand binds to an additional antibody added to the sample being tested. One example of such a ligand includes fluorescein. The additional antibody may be bound to a solid support (e.g., an optical sensing site of the scanning sensor system). The additional antibody binds to the ligand coupled with the antibody that binds in turn to the analyte or alternatively to the labeled analyte, forming a mass complex which allows isolation and measurement of the signal generated by the label coupled with the labeled analyte.

In another type of exemplary competitive immunoassay, the biologically active analyte to be measured may be bound to a solid support (e.g., an optical sensing site of the scanning sensor system), and incubated with both an antibody that binds to the analyte and a sample containing the analyte to be measured. The antibody binds to either the analyte bound to the solid support or to the analyte in the sample, in relative proportions depending on the concentration of the analyte in the sample. The antibody that binds to the analyte bound to the solid support is then bound to another antibody, such as anti-mouse IgC, that is coupled with a label, The amount of signal generated from the label is then detected to measure the amount of antibody that bound to the analyte bound to the solid support. Such a measurement will be inversely proportional to the amount of analyte present in the sample. Such an assay may be used in the scanning sensor system of the present invention.

A wide diversity of labels are available in the art that can be employed for conducting the subject assays. In some embodiments labels are detectable by spectroscopic, photochemical, biochemical, immunochemical, or chemical means. For example, useful nucleic acid labels include fluorescent dyes, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present invention for the labeling of biological components. Suitable labels include enzymes, substrates, cofactors, inhibitors, fluorescent moieties, chemiluminescent moieties, or bioluminescent labels. Labeling agents optionally include, for example, monoclonal antibodies, polyclonal antibodies, proteins, or other polymers such as affinity matrices, carbohydrates or lipids. Detection proceeds by any of the methods described herein, for example, by detecting an optical signal in an optical waveguide. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present invention. Preferred labels include labels that produce an optical signal. Thus, a label includes without limitation any composition detectable by spectroscopic, photochemical, biochemical, immunochemical, electrical, optical, thermal, or chemical means.

In some embodiments the label is coupled directly or indirectly to a molecule to be detected such as a product, substrate, or enzyme, according to methods well known in the art.

As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule is covalently bound to a polymer. The ligand then binds to an anti ligand molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, and umbelliferone. Chemiluminescent compounds include luciferin, and 2,3-dihydrophthalazinediones, such as luminol.

Methods of detecting labels are well known to those of skill in the art. Thus, for example, where the label is a fluorescent label, it may be detected by exciting the fluorochrome with the appropriate wavelength of light and detecting the resulting fluorescence by, for example, a scanning sensor system as described herein. Similarly, enzymatic labels are detected by providing appropriate substrates for the enzyme and detecting the resulting reaction product (e.g., a reaction product capable of producing a detectable optical signal).

In some embodiments the detectable signal may be provided by luminescence sources. "Luminescence" is the term commonly used to refer to the emission of light from a substance for any reason other than a rise in its temperature. In general, atoms or molecules emit photons of electromagnetic energy (e.g., light) when they move from an "excited state" to a lower energy state (usually the ground state); this process is often referred to as "radioactive decay". There are many causes of excitation. If the exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin allowed transitions. If photoluminescence is the result of a spin forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

Suitable chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In a separate embodiment, the present invention provides a method of monitoring one or more pharmacological parameter, for example, Pharmacodynamic (PD) and/or pharmacokinetic (PK) parameters, useful for assessing efficacy and/or toxicity of a therapeutic agent. The method comprises subjecting a sample of bodily fluid from a subject administered with the therapeutic agent to a scanning sensing device for monitoring the one or more pharmacological parameter, the scanning sensing device can be used as described herein to yield detectable signals indicative of the values of the more than one pharmacological parameter from the sample; and detecting the detectable signal generated from said sample of bodily fluid.

In one implementation the samples tested can include a large number of a variety of small molecules (e.g., screening libraries) which are of interest when investigating new drugs. Accordingly, the scanning sensing system described herein is useful for screening libraries of small molecules to investigate their ability to interact with certain biologically active analytes may reveal potential new drugs. Further screening of some or all small molecule candidates may reveal adverse drug effects and toxicity.

In one implementation the samples can include molecules which are tested for toxicity.

In general in another aspect methods of using the scanning sensing systems described herein are provided.

In one embodiment, the light source, for example, an optical switch or an array of light generator elements, couples light into one or more in-coupling waveguides at any given time. The light travels along the waveguides, reaches the optical sensing sites and interacts through the sensor, for example, an optical transducer. The samples are positioned at or near the waveguides. Next, the light leaving the sensor couples into the out-coupling waveguides and travels down the waveguide to its end at an edge of the substrate, for example, a chip facet. Light exiting the out-coupling waveguides is then detected by the different elements of the detector, which can be a detector array.

In another embodiment, scanning sensing of a sample includes delivering a sample suspected of containing a target to be detected to an optical sensing site of the scanning sensor system. Delivering a sample to the system can include pipetting of a fluid to the optical sensing site. Other delivery means can include but are not limited to robotic fluid delivery system or physically depositing a non-fluid or semi-fluid sample at the optical sensing site, either by hand or with the aid of a tool or robot manipulation system. Next, a first light wave produced by the light source is provided to one or more of the plurality of waveguides in optical communication with the optical sensing site. The first light wave is transduced (e.g., measurably changed) by the sensor associated with the optical sensing site to form a second light wave carried back in one or more of the plurality of out-coupling waveguides which are in optical communication with the optical sensing site. Next a measurable change in the second light wave is detected using the detector which is in optical communication with the out-coupling waveguides. Detection of measurable change in the second light waves indicates that the sensor has interacted with the target. It is envisioned that the waveguides described herein can be arranged substantially parallel as illustrated generally in the accompanying figures.

In a further embodiment, scanning sensing includes switching one or more light wave from the light source into the substrate to produce the first light wave in one or more of the waveguides in a controlled and scanning manner.

In another embodiment, the light source includes an optical switch for controlling switching of one or more input light wave. The optical switch can multicast light to a plurality of outputs. The plurality of light waves can be coupled into the sensing substrate to controllably produce the first light wave in one or more of the waveguides.

In one embodiment, all in-coupling waveguides are provided with a first light wave and simultaneous detection of second light waves at each out-coupling waveguide is achieved using a detector that is a photodetector array.

By switching light between waveguides, each waveguide can be individually addressed with a first light wave. The order of addressing the waveguides can be sequential, staggered, random or in any order desired. Rapid scanning of the entire array of optical sensing sites can be achieved with the aid of the photodetector array since any second light wave associated with each out-coupling waveguide can be simultaneously detected.

In various embodiments the method of using the scanning sensing system involves the detection of a substance, including but not limited to a biologically active analyte including a nucleic acid, a protein, an antigen, an antibody, a panel of proteins, a microorganism, a gas, a chemical agent and a pollutant. In a particular embodiment, a single nucleotide polymorphism (SNP) is detected in the target. In one embodiment expression of a gene is detected upon detection of the target.

Systems using planar waveguides for optical detection of SNPs have been described before. For example, single base extension ("SBEX") with planar waveguide fluorescent biosensor technology to detect SNPs has been described by Herron and Tolley in U.S. patent application Ser. No. 10/984,629, filed Nov. 8, 2004 and titled "Single Base Extension." Briefly, total internal reflectance fluorometry (TIRF) can be used in combination with SBEX under real time detection conditions for SNP detection using planar waveguide technology. Evanescent waves generated in a waveguide substrate will only excite fluorescently labeled analyte DNA molecules that are bound to stationary capture oligonucleotides. Herron found that the depth of evanescent wave useful for measurements is within about 300 nm of the sensor surface. The SBEX approach uses a DNA polymerase to incorporate, for example, Cy5 labeled dideoxynucleotriphosphates (dd-NTPs). Additional labels are discussed elsewhere herein.

Identification ("calling") of the single base added to the 3' end of the probe molecule can be done in one of three ways: parallel channels for each of the four bases using a different labeled ddNTP in each channel; sequential SBEX reactions using a different labeled ddNTP in each reaction; or wavelength discrimination of the four possibilities using a different fluorescent label for each ddNTP. The first of these methods may be preferred. SBEX may be used in oligonucleotide genotyping and SNP detection systems, and is advantageous over traditional hybridization assays, for example, due to greater base specificity, production of a covalent bond between the labeled ddNTP and the probe, and simultaneous detection of multiple bases.

By using SBEX on waveguides, simultaneous detection of several different polymorphisms can be done with ease. By patterning the waveguide with different capture sequences, different points in a sequence, for example, a genome, a chromosome and/or a gene, may be assayed. As SBEX only requires a fluorescent label on the ddNTP monomers used, all instances of a particular base will be detected. In order to do the same thing with a traditional DNA hybridization assay, each probe DNA for each capture sequence would have to be fluorescently labeled.

The enzyme-catalyzed reaction has two distinct advantages. First, a stable covalent bond forms between the stationary phase and a labeled monomer, e.g., a Cy5-labeled monomer. This increases the assay sensitivity versus traditional hybridization assays where the fluorescent label is captured by the stationary phase via non-covalent interactions (duplex formation). Optionally a stringent washing step can be employed. Second, the polymerase enzyme incorporates the dideoxynucleotide with high fidelity—due to the replication accuracy of a polymerase, in general only the base that is complementary to the target base will react. SBEX is particularly well suited for planar waveguide technology, benefiting from the increased speed of a washless assay and increased sensitivity provided by kinetic data.

Using SBEX on the waveguide platform, enables a rapid assays (<5 min) results to be performed that is are able to differentiate between single nucleotide polymorphic and wild type sequences at temperatures less than 50° C.

Fluorescence imaging is sensitive to speed, sensitivity, noise and resolution, and each may be optimized for use in the invention, for example, speed may be increased to increase assay times. Base extension may be detected using a CCD camera, a streak camera, spectrofluorometers, fluorescence scanners, or other known fluorescence detection devices, which generally comprise four elements, an excitation source, a fluorophore, a filter to separate emission and excitation photons, and a detector to register emission photons and produce a recordable output, typically an electrical or photographic output.

Polymerase enzymes useful in the invention are known in the art and include, but are not limited to, thermostable polymerases, such as pfu, Taq, Bst, Tfl, Tgo and Tth polymerase, DNA Polymerase I, Klenow fragment, and/or T4 DNA Polymerase. The polymerase may be a DNA-dependent DNA polymerase, a DNA-dependent RNA polymerase, a RNA-dependent RNA polymerase, a RNA-dependent DNA polymerase or a mixture thereof, depending on the template, primer and NTP used. The polymerase may or may not have proofreading activity (3' exonuclease activity) and/or 5' exonuclease activity.

The capture molecule and/or the analyte molecule of the invention may be any nucleic acid, including, but not limited to, DNA and/or RNA and modifications thereto known in the art, and may incorporate 5'-O-(1-thio)nucleoside analog triphosphates, .alpha.-thiotriphosphate, 7-Deaza-.alpha.-thiotriphosphate, N6-Me-.alpha.-thiotriphosphate, 2'-O-Methyl-triphosphates, morpholino, PNA, aminoalkyl analogs, and/or phosphorotioate.

In one embodiment immunoassays can be used with the present method of using the scanning sensing system. The optical sensing site of the method of using the scanning sensing system of the invention can be adapted to support an immunoassay, for example, by including one or more immunoassay reagent at or within the optical sensing site. In this embodiment an interaction between the optical sensing site and a sample being tested for a biologically active analyte can include an immunoassay conducted at the optical sensing site. As such, the optical sensing site interacting with the biologically active analyte can include an outcome of an immunoassay. In this manner, presence or absence of the analyte can be determined. Additionally the amount of analyte can be quantified. In one embodiment the immunoassay supported is a fluorescent assay. It is envisioned that the immunoassay can be a competitive or non-competitive immunoassay. In one embodiment the immunoassay supported in an ELISA.

It is envisioned that a variety of instrumentation relating to biological or environmental sample preparation, handling and analysis can be used in conjunction with the system and methods described herein. Examples of such instrumentation include but are not limited to a cell sorter, a DNA amplification thermal cycler, or a chromatography machine (e.g., GC or HPLC). Such instrumentation is well known to those skilled in the art. It is envisioned that a robotic interface could be used between the scanning sensing system of the present invention and various instrumentation relating to biological or environmental sample preparation, handling and analysis.

The system and methods described herein may be used in a range of applications including biomedical and genetic research as well as clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839. The nucleic acid arrays may be used in many other applications including detection of genetic diseases such as cystic fibrosis or diagnosis of HIV, as disclosed in U.S. Pat. No. 6,027,880 and U.S. Pat. No. 5,861,242. Genetic mutations may be detected by sequencing by hybridization. In one embodiment, genetic markers may be sequenced and mapped using Type-IIs restriction endonucleases as disclosed in U.S. Pat. No. 5,710,000.

Other applications include chip based genotyping, species identification and phenotypic characterization, as described in U.S. Pat. No. 6,228,575. Still other applications including diagnosing a cancerous condition or diagnosing viral, bacterial, and other pathological or nonpathological infections, are described in U.S. Pat. No. 5,800,992. A further application includes chip based single nucleotide polymorphism (SNP) detection as described in U.S. Pat. No. 6,361,947.

Gene expression may be monitored by hybridization of large numbers of mRNAs in parallel using high density arrays of nucleic acids in cells, such as in microorganisms such as yeast, as described in Lockhart et al., *Nature Biotechnology*, 14:1675-1680 (1996). Bacterial transcript imaging by hybridization of total RNA to nucleic acid arrays may be conducted as described in Saizieu et al., *Nature Biotechnol-* ogy, 16:4548 (1998). Accessing genetic information using high density DNA arrays is further described in Chee, *Science* 274:610-614 (1996).

A non-limiting list of potential application suitable for sensing using the systems and methods described herein includes: pathogens detection and classification; chemical/biological warfare real-time detection; chemical concentration control; dangerous substance (e.g., gas, liquid) detection and alarm; sugar and insulin levels detection in diabetic patients; pregnancy testing; detection of viral and bacterial infectious diseases (e.g. AIDS, Bird Flu, SARS, West Nile virus); environmental pollution monitoring (e.g., water, air); and quality control in food processing.

The working system described here can also be a subsystem within a much larger bio-analysis system. The bio-analysis system could include all the aspects of sample preparation prior to the optical scanning, the post processing of data collected in the optical scanning phase and finally decision making based on these results. Sample preparation may include steps such as: extraction of the sample from the tested subject (human, animal, plant environment etc.); separation of different parts of the sample to achieve higher concentration and purity of the molecules under investigation; sample amplification (e.g. through PCR); attachment of fluorescence tags or markers to different parts of the sample; and spotting of the sample into the sensing chip. The post processing of the collected data may include: normalization; background and noise reduction; and statistical analysis such as averaging over repeated tests or correlation between different tests. The decision making may include: testing against a predefined set of rules and comparison to information stored in external data-bases.

The applications and uses of the scanning sensing systems described herein can produce one or more result useful to diagnose a disease state of an individual, for example, a patient. In one embodiment, a method of diagnosing a disease comprises reviewing or analyzing data relating to the presence and/or the concentration level of a target in a sample. A conclusion based review or analysis of the data can be provided to a patient, a health care provider or a health care manager. In one embodiment the conclusion is based on the review or analysis of data regarding a disease diagnosis. It is envisioned that in another embodiment that providing a conclusion to a patient, a health care provider or a health care manager includes transmission of the data over a network.

Accordingly, business systems and methods using the scanning sensing systems and methods described herein are provided.

One aspect of the invention is a business method comprising screening patient test samples for the presence or absence of a biologically active analyte to produce data regarding the analyte, collecting the analyte data, providing the analyte data to a patient, a health care provider or a health care manager for making a conclusion based on review or analysis of the data regarding a disease diagnosis. In one embodiment the conclusion is provided to a patient, a health care provider or a health care manager includes transmission of the data over a network.

Figure 8:
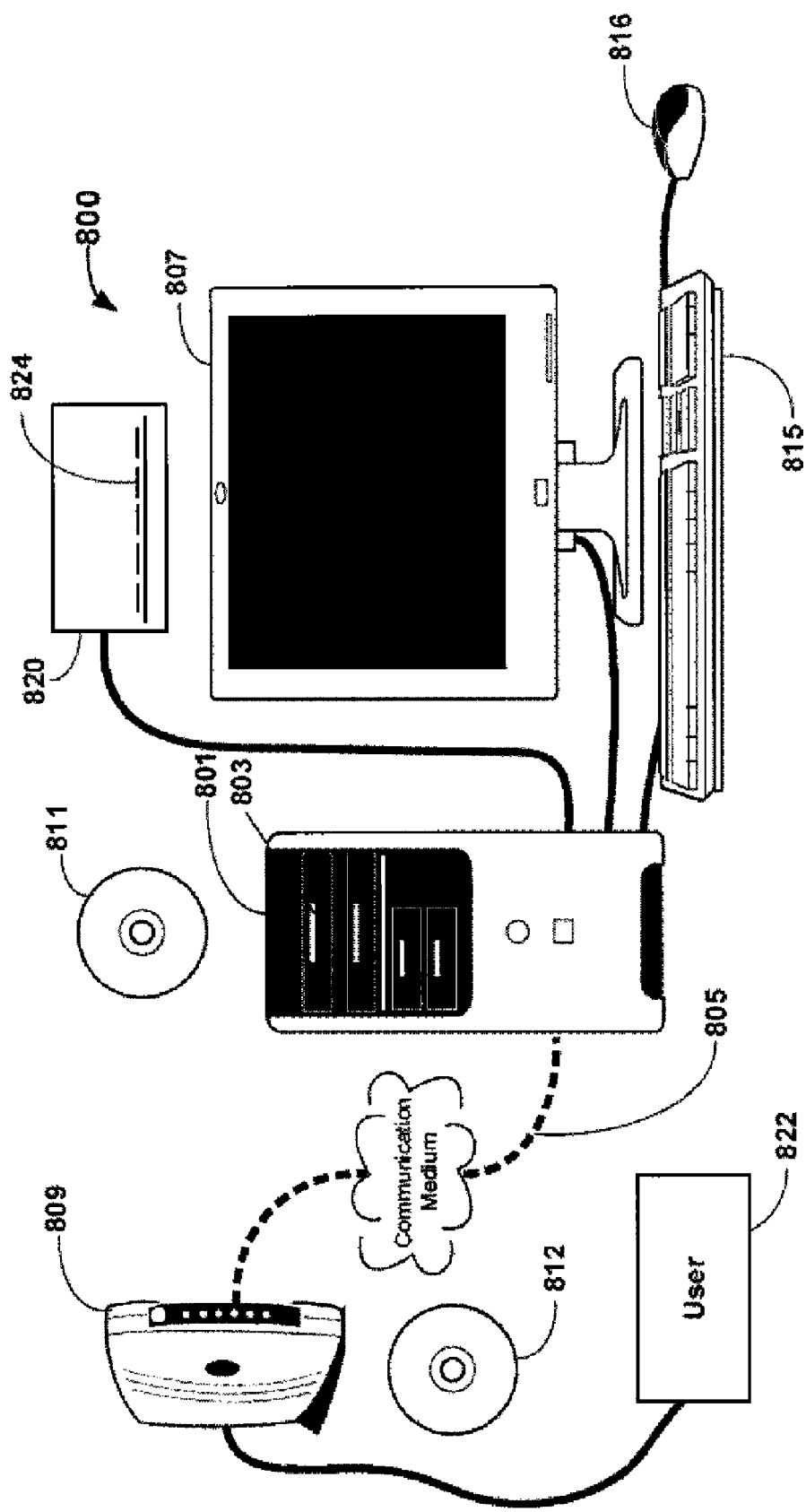
FIG. 8 is a block diagram showing a representative example logic device in communication with an apparatus for use with the scanning sensing system of the invention.

Accordingly FIG. 8 is a block diagram showing a representative example logic device through which reviewing or analyzing data relating to the present invention can be achieved. Such data can be in relation to a disease, disorder or condition in an individual. FIG. 8 shows a computer system (or digital device) 800 connected to an apparatus 820 for use with the scanning sensing system 824 to, for example, produce a result. The computer system 800 may be understood as a logical apparatus that can read instructions from media 811 and/or network port 805, which can optionally be connected to server 809 having fixed media 812. The system shown in FIG. 8 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present invention can be transmitted over such networks or connections for reception and/or review by a party 822. The receiving party 822 can be but is not limited to a patient, a health care provider or a health care manager.

In one embodiment, a computer-readable medium includes a medium suitable for transmission of a result of an analysis of an environmental or biological sample. The medium can include a result regarding a disease condition or state of a subject, wherein such a result is derived using the methods described herein.

Kits comprising reagents useful for performing the methods described herein are also provided.

In some embodiments, a kit comprises scanning sensing system as described herein and reagents for detecting a target in the sample. The kit may optionally contain one or more of the following: one or more fluorescent or luminescent molecular tag, and one or more biologically active analyte including a nucleic acid, protein, microorganism or chemical agent.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target biologically active analyte including nucleic acid, protein, microorganism, gas, chemical agent or pollutant.

Figure 9:
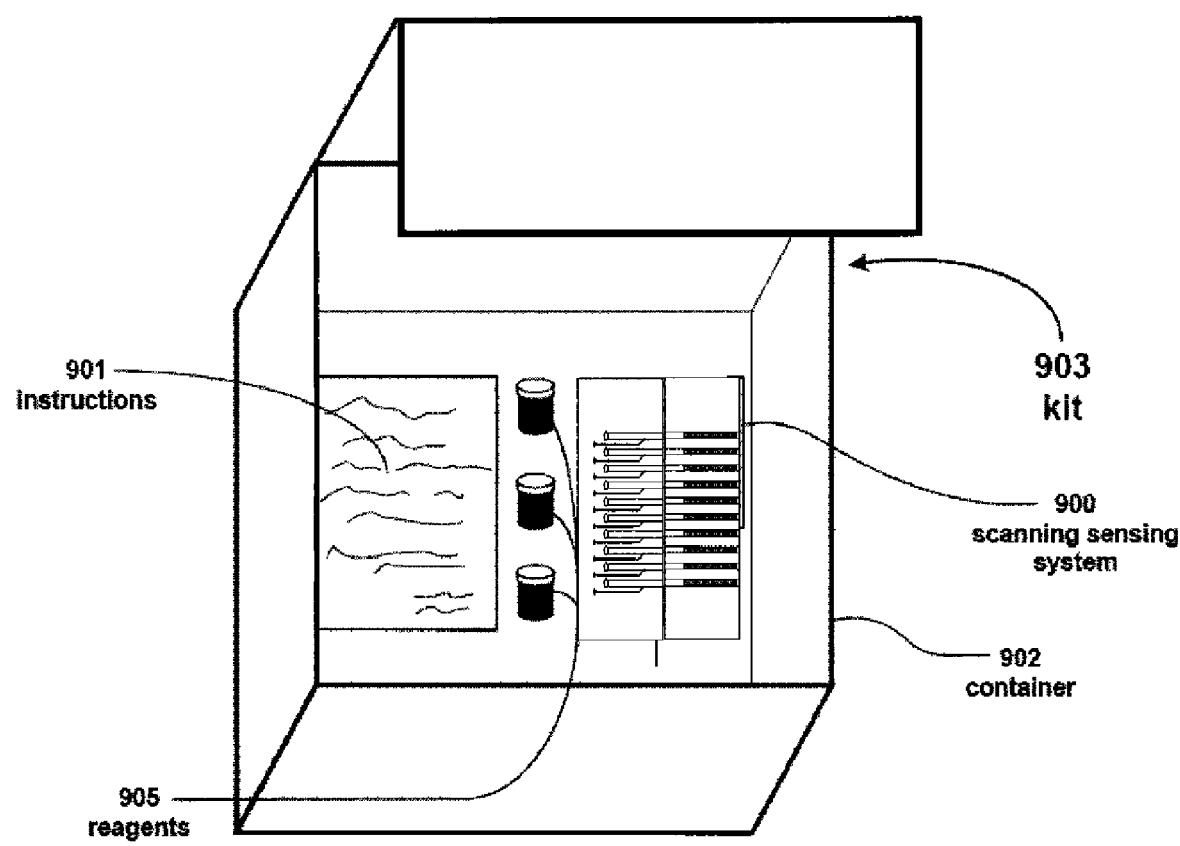
FIG. 9 is a block diagram showing a representative example of a kit.

As described herein and shown in an illustrative example in FIG. 9, in certain embodiments a kit 903 can include a housing or container 902 for housing various components. As shown in FIG. 9, and described herein, the kit 903 can optionally include instructions 901 and reagents 905, for example, DNA hybridization or immunoassay reagents. Other embodiments of the kit 903 are envisioned wherein the components include various additional features described herein.

In one embodiment, a kit for assaying a sample for a target includes a scanning sensor system including a light source, a detector, and a substrate. The substrate can include a plurality of substantially parallel in-coupling waveguides and a plurality of substantially parallel out-coupling waveguides as described herein. The system can further include a plurality of optical sensing sites. The optical sensing sites are in optical communication with one or more waveguides. The kit further includes packaging and instructions for use of the system.

In one embodiment, the kit includes a scanning sensor system that is a planar lightwave circuit (PLC).

In general, in another aspect methods of manufacturing a scanning sensing system for assaying a sample for a target are provided. In one embodiment the system is a PLC.

The starting material or substrate for manufacturing PLC devices is a wafer usually made of Silicon (Si) or Silica (SiO2). The most common wafer diameters in use are 4", 6" and 8". The manufacturing process for PLC devices involves two basic processes namely, deposition and etching. A short description of each of them is given below.

In certain embodiments the methods of manufacturing the systems described herein can include, but are not limited to laser writing, UV writing and photonic band-gap waveguide methods. The manufacturing process in some embodiments includes one or more steps of deposition, masking and etching.

Deposition:

In the deposition step a layer of well defined material having well controlled thickness is deposited across the entire wafer. The most common material used for waveguide layer deposition is Silica (SiO2) also known as glass. The optical properties of the Silica (mainly its refractive index) is controlled by the amount of doping (Ge, P, and B etc.) introduced during the deposition. Other materials such as silicon, glass, epoxy, lithium niobate, indium phosphide and SiON (Silicon OxyNitride) and its derivatives are also used. For the cladding layer, materials can include but are not limited to silicon, silica (SiO2), glass, epoxy, lithium niobate and indium phosphide.

The deposition step is done using several technologies such as PECVD (Plasma-Enhanced Chemical Vapor Deposition), LPCVD (Low Pressure CVD), APCVD (Atmospheric pressure CVD), FHD (Flame Hydrolysis Deposition) and others well known in the art.

Figure 10A:
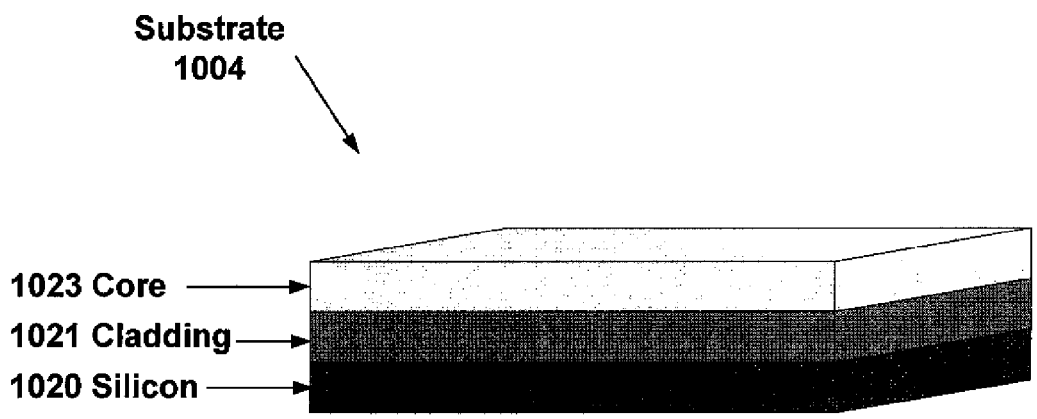
FIGS. 10A-D are schematics illustrating a representative manufacturing process for the substrate and waveguides of the invention.

FIG. 10A illustrates an exemplary substrate 1004 as a schematic structure created after two consecutive deposition steps of a cladding 1021 layer and a core 1023 layer over a silicon 1020 layer, which can be a wafer. As mentioned above, these two layers differ in the refraction index which is achieved by using different levels of doping. Typical thicknesses for the different layers are: Cladding up to about 20 μm and core up to 6 μm. The thickness of the silicon 1020 wafer can range from about 0.5 mm to 1 mm.

Figure 10B:
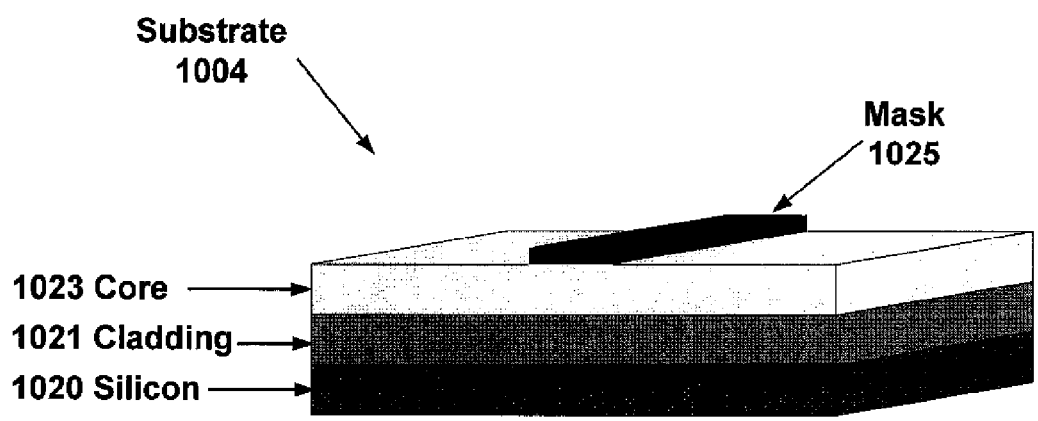

Masking:

Following the deposition and before the etching step, the desired two-dimensional structure of the PLC device is transferred to the deposited wafer by masking the areas not to be etched away. The masking is done in several steps involving covering the wafer with light sensitive material, exposing it to light through lithographic masks and removing the exposed material leaving in place the mask. The result of such steps is shown in FIG. 10B where a mask 1025 is shown on top of the core 1023 layer of the substrate 1004.

Figure 10C:
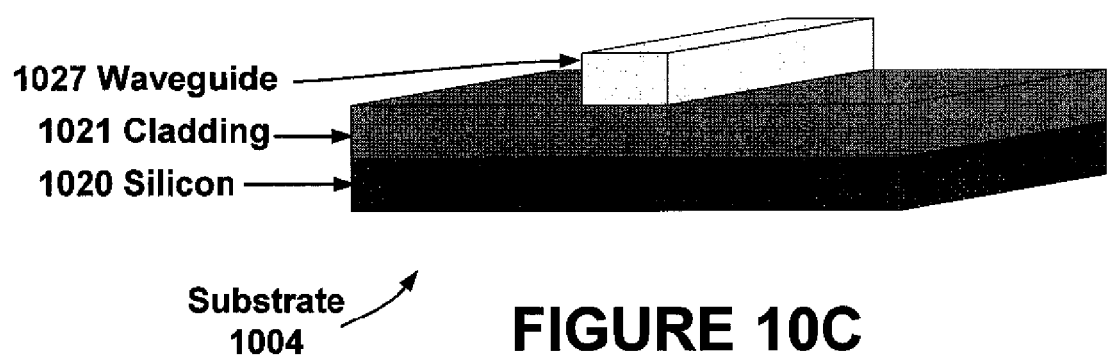

Etching:

In the etching step, material at the un-masked areas is removed from the top core 1023 layer of the substrate (see FIG. 10C). The etching rate is a known parameter, therefore the etching depth can be controlled by time. The two most common techniques for etching are wet-etching and Reactive-Ion-Etching (RIO). FIG. 10C shows the results of the etching step which results in a waveguide 1027.

Figure 10D:
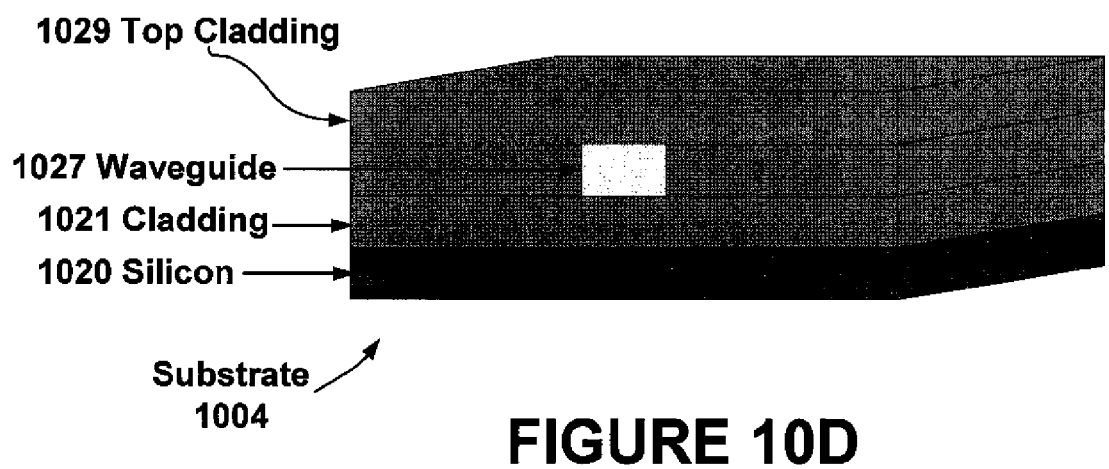

After the etching step, an over-cladding or top cladding 1029 layer is created using a deposition step similar to the one described above. The results are shown in FIG. 10D. As shown in FIG. 10D, the resulting waveguide 1027 can be surrounded by a top cladding 1029 and a cladding 1021 over a silicon 1020 layer.

The above steps can be repeated to create several waveguide layers one on top of the other. In this case, a planarization step may be required between one waveguide layer and the other. This is done using a technique known as Chemical Mechanical Planarization (CMP).

Figure 11:
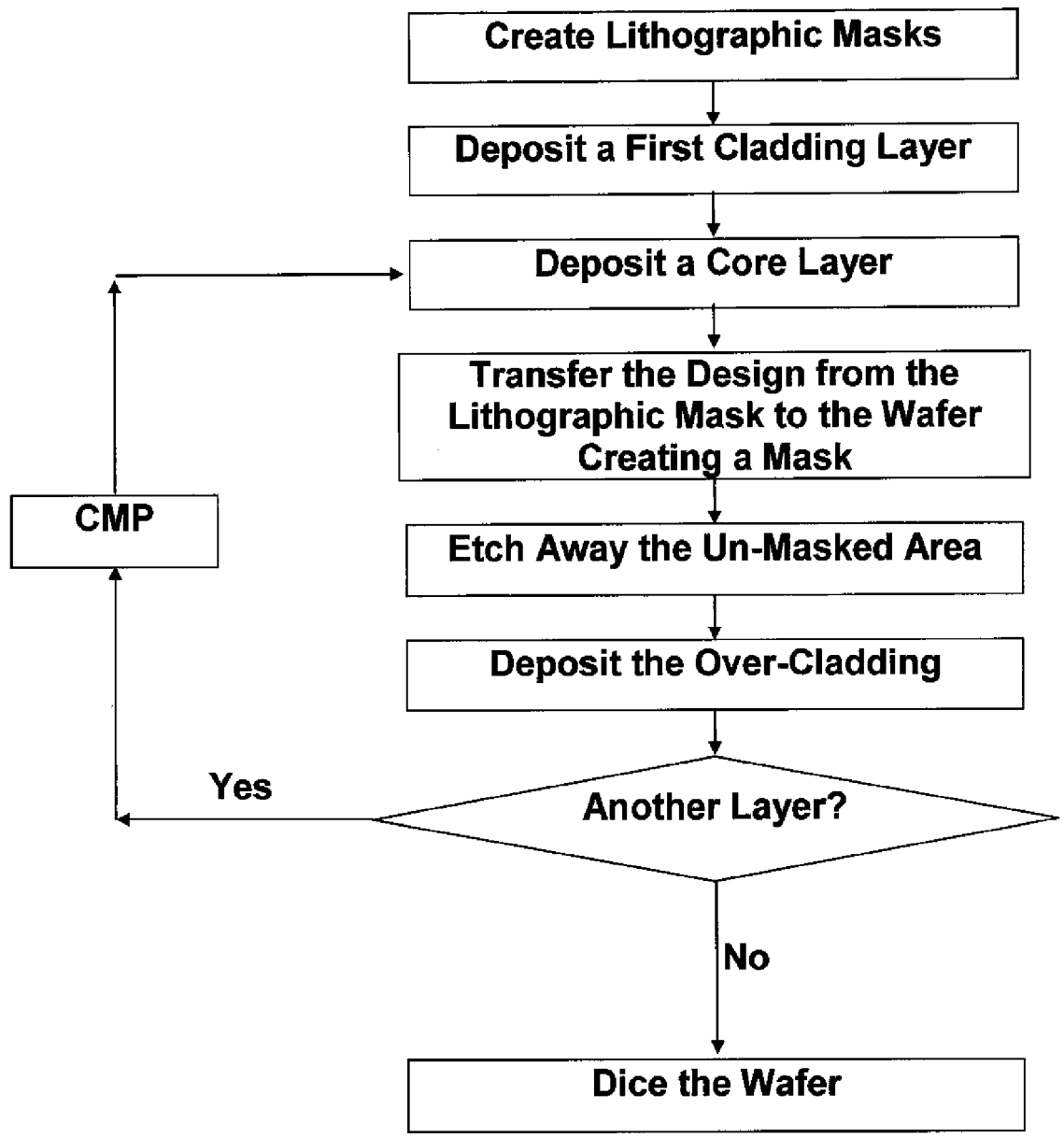
FIG. 11 is a flow chart showing a representative manufacturing process for the substrate.

When the wafer processing is completed, it can be diced into the individual chips. An exemplary simplified flow-chart of the manufacturing process is shown in FIG. 11.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A scanning sensor system for detecting a biologically active analyte comprising:
a light source;
a detector;
a substrate comprising a plurality of waveguides and a plurality of optical sensing sites in optical communication with one or more of the waveguides, wherein the optical sensing sites comprise wells, further wherein the waveguides are multi-mode; and
at least one adapter configured to couple with the substrate and provide optical communication between the light source, the waveguides of the substrate, and the detector.

2. The system of claim 1, wherein the substrate and the at least one adapter are substantially planar and comprise a planar lightwave circuit.

3. The system of claim 1, wherein the at least one adapter is further configured to removably couple with the substrate.

4. The system of claim 1, wherein the at least one adapter is further coupled to at least one of the light source and the detector.

5. The system of claim 1, wherein the at least one adapter is a single adapter further coupled to the light source and the detector.

6. The system of claim 4, wherein the coupling is by fiber optic.

7. The system of claim 5, wherein the adapter comprises a plurality of edges and wherein coupling to the light source and the detector comprises coupling to a first edge of the adapter and coupling to the substrate comprises coupling at a second edge of the adapter.

8. The system of claim 5, wherein the adapter comprises a plurality of optical elements comprising at least one lens and at least one filter, wherein the plurality of optical elements are configured to manipulate and couple light from the light source to the substrate and further configured to manipulate and couple light from the substrate to the detector.

9. The system of claim 5, wherein the plurality of waveguides comprise in-coupling waveguides and out-coupling waveguides.

10. The system of claim 9, wherein the in-coupling waveguides are coupled to the out-coupling waveguides through a combiner.

11. The system of claim 10, wherein the substrate further comprises at least one combiner.

12. The system of claim 10, wherein the adapter further comprises at least one combiner.

13. The system of claim 1, wherein the at least one adapter is a single adapter, the plurality of waveguides comprise in-coupling waveguides and out-coupling waveguides, wherein the in-coupling waveguides are coupled to the out-coupling waveguides through a combiner, wherein the light source comprises a light generator element coupled to at least one in-coupling waveguide, and wherein the detector comprises a detector element coupled to at least one out-coupling waveguide.

14. The system of claim 1, wherein the optical sensing site further comprises a sensor configured to transduce a first light wave generated by the light source in a waveguide, resulting in a second light wave in the same waveguide, the second light wave being detectable by the detector.

15. The system of claim 14, wherein the plurality of waveguides comprise in-coupling waveguides coupled to out-coupling waveguides by way of combiners, and wherein the first light wave is carried by an in-coupling waveguide and the second light wave is carried by an out-coupling waveguide.

16. The system of claim 15, wherein both the adapter and substrate comprise inter-coupling optically communicating in-coupling waveguides and out-coupling waveguides and wherein the substrate further comprises the combiners.

17. The system of claim 14, wherein the sensor comprises a biologically active analyte in a sample, and wherein a measurable change in the first light wave results when the sensor discriminates or interacts with the biologically active analyte.

18. The system of claim 1, wherein the wells of the optical sensing sites support an immunoassay.

19. The system of claim 18, wherein the immunoassay supported is an enzyme-linked immunosorbent assay (ELISA).

20. The system of claim 18, wherein the immunoassay supported is a fluorescent immunoassay.

21. The system of claim 1, wherein the sensor is selected from the group consisting of a fluorescence well, an absorption cell, an interferometric sensor, a diffractive sensor and surface plasmon resonance sensor.

22. The system of claim 1, wherein the biologically active analyte is selected from the group consisting of a nucleic acid, a protein, an antigen, an antibody, a lipid, a polysaccharide, a cell, a tissue, a microorganism, a gas, a chemical agent and a pollutant.

23. The system of claim 22, wherein the nucleic acid is produced via an amplification reaction.

24. The system of claim 1, wherein the waveguides are single-mode.

25. The system of claim 1, wherein the waveguides are single-mode in the vertical dimension and multi-mode in the lateral dimension.

26. The system of claim 1, wherein the number of optical sensing sites is greater than 10.

27. The system of claim 1, wherein the number of optical sensing sites is greater than 200.

28. The system of claim 1, wherein the number of optical sensing sites is greater than 5,000.

29. The system of claim 1, wherein the light source comprises a chip containing an array of light generators coupled to an array of waveguides.

30. The system of claim 1, wherein the light source comprises a passive light source.

31. The system of claim 30, wherein the light source is a passive 1×N splitter with N being between 1 and 1000.

32. The system of claim 1, wherein the light source comprises a switchable light source.

33. The system of claim 32, wherein the switchable light source comprises a dynamic light source.

34. The system of claim 32, wherein the switchable light source is an optical switch comprising a light generator coupled to one or more input of the optical switch.

35. The system of claim 34, wherein the optical switch further comprises a branched architecture.

36. The system of claim 35, wherein the optical switch further comprises one or more inputs and multiple outputs.

37. The system of claim 36, wherein the optical switch comprises greater than about 10 outputs.

38. The system of claim 36, wherein the optical switch comprises greater than about 100 outputs.

39. The system of claim 36, wherein the optical switch comprises greater than about 1,000 outputs.

40. The system of claim 36, wherein the optical switch comprises substantially between 20 and 200 outputs.

41. The system of claim 34, wherein the light generator provides variable wavelengths of light.

42. The system of claim 34, wherein the light generator is selected from the group consisting of a broad-band source, a source with one or more discrete spectral lines and a tunable source.

43. The system of claim 1, wherein the light source is butt-coupled to one or more of the at least one adapter.

44. The system of claim 1, wherein the light source comprises one or more waveguide and is evanescently coupled to the at least one adapter through a proximate arrangement of the one or more light source waveguide and one or more waveguide of the at least one adapter.

45. The system of claim 1, wherein the detector is a photodetector array.

46. The system of claim 1, wherein the detector is a plurality of detectors.

47. The system of claim 46, wherein two or more detectors are coupled to and in optical communication with one or more waveguide of the at least one adapter at one or more edges of the at least one adapter.

48. The system of claim 1, wherein the system further comprises a thermal transfer element in thermal communication with the substrate.

49. The system of claim 48, wherein the thermal transfer element is a thermoelectric cooler.

50. The system of claim 1, wherein each optical sensing site comprises a thermal transfer element in thermal communication with the optical sensing site.

51. The system of claim 50, wherein the thermal transfer element comprises a thin-film heater.

52. The system of claim 50, wherein each optical sensing site further comprises a thermistor in thermal communication with the optical sensing site.

53. The system of claim 1, wherein the substrate further comprises one or more microchannel and one or more reservoirs in fluid communication with one or more optical sensing site.

54. The system of claim 1, wherein the system further comprises a fluidics layer coupled to the substrate and comprising one or more microchannel and one or more reservoirs in fluid communication with one or more optical sensing site.

55. A kit for assaying a sample for a biologically active analyte comprising:
    a scanning sensor system comprising a light source, a detector, a substrate comprising a plurality of waveguides and a plurality of optical sensing sites in optical communication with one or more waveguide of the substrate, wherein the optical sensing sites comprise wells, further wherein the waveguides are single-mode in the vertical dimension and multi-mode in the lateral dimension, and at least one adapter configured to couple with the substrate and provide optical communication between the light source, the waveguides of the substrate, and the detector;

packaging; and instructions for use of the system.

56. The kit of claim 55, wherein the adapter and substrate comprises a planar lightwave circuit.

57. The kit of claim 55, wherein the optical sensing sites comprise a sensor for an immunoassay, and wherein the kit further comprises one or more immunoassay reagents.

58. A scanning sensor system for detecting a biologically active analyte comprising:
- a light source;
- a detector;
- a substrate comprising a plurality of waveguides and a plurality of optical sensing sites in optical communication with one or more of the waveguides, wherein the optical sensing sites comprise wells, further wherein the optical sensing site further comprises a sensor configured to transduce a first light wave generated by the light source in a waveguide, resulting in a second light wave in the same waveguide, the second light wave being detectable by the detector; and
- at least one adapter configured to couple with the substrate and provide optical communication between the light source, the waveguides of the substrate, and the detector, wherein the plurality of waveguides comprise in-coupling waveguides coupled to out-coupling waveguides by way of combiners, and wherein the first light wave is carried by an in-coupling waveguide and the second light wave is carried by an out-coupling waveguide.

59. A scanning sensor system for detecting a biologically active analyte comprising:
- a light source;
- a detector;
- a substrate comprising a plurality of waveguides and a plurality of optical sensing sites in optical communication with one or more of the waveguides, wherein the optical sensing sites comprise wells, further wherein the waveguides are single-mode in the vertical dimension and multi-mode in the lateral dimension; and
- at least one adapter configured to couple with the substrate and provide optical communication between the light source, the waveguides of the substrate, and the detector.

60. A scanning sensor system for detecting a biologically active analyte comprising:
- a light source;
- a detector;
- a substrate comprising a plurality of waveguides and a plurality of optical sensing sites in optical communication with one or more of the waveguides, wherein the optical sensing sites comprise wells; and
- at least one adapter configured to couple with the substrate and provide optical communication between the light source, the waveguides of the substrate, and the detector, wherein the light source is butt-coupled to one or more of the at least one adapter.

61. The system of claim 1, wherein the waveguides are single-mode in at least one dimension.

* * * * *